US005667988A

United States Patent [19]
Barbas et al.

[11] Patent Number: 5,667,988
[45] Date of Patent: Sep. 16, 1997

[54] METHODS FOR PRODUCING ANTIBODY LIBRARIES USING UNIVERSAL OR RANDOMIZED IMMUNOGLOBULIN LIGHT CHAINS

[75] Inventors: Carlos F. Barbas, San Diego; Dennis R. Burton; Richard A. Lerner, both of La Jolla, all of Calif.

[73] Assignee: The Scripps Research Institute, La Jolla, Calif.

[21] Appl. No.: 300,386

[22] Filed: Sep. 2, 1994

Related U.S. Application Data

[63] Continuation-in-part of Ser. No. 174,674, Dec. 28, 1993, abandoned, which is a continuation-in-part of Ser. No. 12,566, Feb. 2, 1993, abandoned, Ser. No. 954,148, Sep. 30, 1992, abandoned, and Ser. No. 826,623, Jan. 27, 1992.

[51] Int. Cl.⁶ .................. C07K 16/00; C12N 15/00
[52] U.S. Cl. ............... 435/69.1; 435/70.21; 435/71.1; 530/387.3
[58] Field of Search .................. 435/69.1, 70.21, 435/71.1; 530/387.3

[56] References Cited

U.S. PATENT DOCUMENTS 5,223,409  6/1993  Ladner .
5,403,484  4/1995  Ladner .

OTHER PUBLICATIONS

Hexam et al, Autoimmunity, 17:167, 1994 (Seq. avail. Jun. 1993).
Portalano, J. Immunol., 151:2839, 1993.
Janme et al., Endocrinology, 135: 16, 1994.
Constante et al., Endocrinology, 135:25, 1994.
Berkower, et al., J. Virology, 65: 5983–5990 (1991).
Broliden, et al., Immunology, 73: 371–376 (1991).
Burton, et al., PNAS, USA, 88: 10134–10137 (1991).
D'Souza, et al., AIDS, 1061–1070 (1991).
Gorny, et al., PNAS, USA, 88: 3238–3242 (1991).
Ho, et al., J. Virology, 65: 489–493 (1991).
Ho, et al., PNAS, USA, 88: 8949–8952 (1991).
Jackson, et al., Lancet, Sep. 17, 1988, pp. 647–651.
Kang, et al., PNAS, USA, 88: 6171–6175 (1991).
Karpas, et al., PNAS, USA, 87: 7613–7617 (1990).
Karwowska, et al., AIDS Res. and Human Retroviruses, 8: 1099–1106 (1992).
Laman, et al., J. Virol., 66: 1823–1831 (1992).
Linsley, et al., J. Virol., 62: 3695–3702 (1988).
McKeating, et al., AIDS, 3: 777–784 (1989).
Nara, et al., AIDS Res. and Human Retroviruses, 3: 283–302 (1987).
Nara, et al., FASEB J., 5: 2437–2455 (1991).
Posner, et al., J. Immunol., 146: 4325–4332 (1991).
Skinner, et al., J. Virol., 62: 4195–4200 (1988).
Steimer, et al., Science, 254: 105–108 (1991).
Takeda, et al., J. Clin. Invest., 89: 1952–1957 (1992).
Thali, et al., J. Virol., 65: 6188–6193 (1991).
Tilley, et al., AIDS Res. and Human Retroviruses, 8: 461–467 (1992).
Tilley, et al., Res. Virol., 142: 247–259 (1991).
Wahlberg, et al., AIDS Res. and Human Retroviruses, 7: 983–990 (1991).
Kang, et al., "Antibody Redesign by Chain Shuffling from Random Combinatorial Immunoglobulin Libraries", Proc. Natl. Acad. Sci., USA, 88: 11120–11123 (1991).
Barbas, et al., "Semisynthetic Combinatorial Antibody Libraries: A Chemical Solution to the Diversity Problem", Proc. Natl. Acad. Sci., USA, 89: 4457–4461 (1992).
Persson, et al., "Generation of Diverse High–Affinity Human Monoclonal Antibodies by Repertoire Cloning", Proc. Natl. Acad. Sci., USA, 88: 2432–2436 (1991).
Gallop, et al., "Applications of Combinatorial Technologies to Drug Discovery. 1. Background and Peptide Combinatorial Libraries", J. of Medicinal Chem., 37: 1233–1251 (1994).
Kipps, et al., "Autoantibody–Associated k Light Chain Variable Region Gene Expressed in Chronic Lymphocytic Leukemia with Little or No Somatic Mutation", J. Exp. Med., 167: 840–852 (1988).
Hay, et al., "Framework Peptides from xIIIb Reheumatoid Factor Light Chains with Binding Activity for Aggregated IgG", Eur. J. Immunol., 21: 1837–1841 (1991).
Higuchi, "Using PCR to Engineer DNA", 1989, PCR Technology, Henry A. Erlich, ed., pp. 61–70, Stockton Press.
Barbas, et al., "Assembly of Combinatorial Antibody Libraries on Phage Surfaces: The Gene III Site", Proc. Natl. Acad. Sci., USA, 88: 7978–7982 (1991).
Cwirla, et al., "Peptides on Phage: A Vast Library of Peptides for Identifying Ligands", Proc. Natl. Acad. Sci., USA, 87: 6378–6382 (1992).
Devlin, et al., "Random Peptide Libraries: A Source of Specific Protein Binding Molecules", Science, 249: 404–406 (1990).
Kang, et al., "Linkage of Recognition and Replication Fundtions by Assembling Combinatorial Antibody Fab Libraries Along Phage Surfaces", Proc. Natl. Acad. Sci., USA, 88: 4363–4366 (1991).
O'Neil, et al., "Design of DNA–Binding Peptides Based on the Leucine Zipper Motif", Science, 249: 774–778 (1990).
Roberts, et al., "Protease Inhibitor Display M13 Phage: Selection of High–Affinity Neutrophil Elastase Inhibitors", Gene, 121: 9–15 (1992).

(List continued on next page.)

Primary Examiner—Frank C. Eisenschenk
Attorney, Agent, or Firm—Thomas Fitting; Emily Holmes

[57] ABSTRACT

The present invention describes methods for producing antibody libraries, and particularly for increasing antibody library diversity by inducing mutagenesis within the CDR regions of immunoglobulin heavy or light chains that are displayed on the surface of filamentous phage particles comprising the library. The invention also describes oligonucleotides useful for increasing the library diversity, and universal light chains useful in the library production methods.

3 Claims, 2 Drawing Sheets

OTHER PUBLICATIONS

Roberts, et al., "Directed Evolution of a Protein: Selection of Potent Neutrophil Elastase Inhibitors Displayed on M13 Fusion Phage", *Proc. Natl. Acad. Sci., USA*, 89: 2429–2433 (1992).

Scott and Smith, "Searching for Peptide Ligands with an Epitope Library", *Science*, 249: 386–390 (1990).

Barbas et al., *Methods: A Companion to Methods in Enzymology*, 2:119–124 (1991).

Huse et al., *Science*, 246:1275–1281 (1989).

McCafferty et al., *Nature*, 348:552–554 (1990).

METHODS FOR PRODUCING ANTIBODY LIBRARIES USING UNIVERSAL OR RANDOMIZED IMMUNOGLOBULIN LIGHT CHAINS

CROSS-REFERENCE TO RELATED APPLICATION

This application is a continuation-in-part application of Ser. No. 08/174,674, now abandoned, filed Dec. 28, 1993, which is a continuation-in-part application of Ser. Nos. 08/012,566, now abandoned, filed Feb. 2, 1993, 07/954,148, now abandoned, filed Sep. 30, 1992 and 07/826,623, filed Jan. 27, 1992, the disclosures of which are hereby incorporated by reference.

This invention was made with government support under Contract Nos. AI 33292 and CA 27489 by The National Institutes of Health. The government has certain rights in the invention.

TECHNICAL FIELD

The present invention relates generally to the field of protein biochemistry and immunology, and relates specifically to methods for the preparation of heterodimeric immunoglobulin molecules containing heavy and light variable chain polypeptides.

BACKGROUND

Large libraries of wholly or partially synthetic antibody combining sites, or paratopes, have been constructed utilizing filamentous phage display vectors, referred to as phagemids, yielding large libraries of monoclonal antibodies having diverse and novel immunospecificities. The technology uses a filamentous phage coat protein membrane anchor domain as a means for linking gene-product and gene during the assembly stage of filamentous phage replication, and has been used for the cloning and expression of antibodies from combinatorial libraries. Kang et al., *Proc. Natl. Acad. Sci., USA*, 88:4363–4366 (1991). Combinatorial libraries of antibodies have been produced using both the cpVIII membrane anchor (Kang et al., supra) and the cpIII membrane anchor (Barbas et al., proc. *Natl. Acad. Sci., USA*, 88:7978–7982 (1991)).

The diversity of a filamentous phage-based combinatorial antibody library can be increased by shuffling of the heavy and light chain genes (Kang et al., *Proc. Natl. Acad. Sci., USA*, 88:11120–11123, 1991), by altering the complementarity determining region 3 (CDR3) of the cloned heavy chain genes of the library (Barbas et al., *Proc. Natl. Acad. Sci., USA*, 89:4457–4461, 1992), and by introducing random mutations into the library by error-prone polymerase chain reactions (PCR) (Gram et al., *Proc. Natl. Acad. Sci., USA*, 89:3576–3580, 1992).

Mutagenesis of proteins has been utilized to alter the function, and in some cases the binding specificity, of a protein. Typically, the mutagenesis is site-directed, and therefore laborious depending on the systematic choice of mutation to induce in the protein. See, for example Corey et al., *J. Amer. Chem. Soc.*, 114:1784–1790 (1992), in which rat trypsins were modified by site-directed mutagenesis. Partial randomization of selected condos in the thymidine kinase (TK) gene was used as a mutagenesis procedure to develop variant TK proteins. Munir et al., *J. Biol. Chem.*, 267:6584–6589 (1992).

There continues to be a need for methods to increase the repertoire of possible antibody molecules from which to manipulate useful binding functions, including heavy chain and light chain immunoglobulin polypeptides.

BRIEF DESCRIPTION OF THE INVENTION

It has now been discovered that the phagemid display technology can be improved by manipulations of the immunoglobulin light chain to prepare diverse libraries of immunoglobulin specificities. In particular, it is shown that the immunoglobulin light chain variable domain can be randomized in its complementarity determining regions (CDR) by random mutagenesis to yield larger and more diverse libraries of light chains from which to draw novel and useful immunospecificities.

Thus, in one embodiment, the invention describes a method for inducing mutagenesis in a complementarity determining region (CDR) of an immunoglobulin light chain gene for the purpose of producing light chain gene libraries for use in combination with heavy chain genes and gene libraries to produce antibody libraries of diverse and novel immunospecificities. The method comprises amplifying a CDR portion of an immunoglobulin light chain gene by polymerase chain reaction (PCR) using a PCR primer oligonucleotide, where the oligonucleotide has 3' and 5' termini and comprises:

a) a nucleotide sequence at its 3' terminus capable of hybridizing to a first framework region of an immunoglobulin light chain gene;

b) a nucleotide sequence at its 5' terminus capable of hybridizing to a second framework region of the immunoglobulin light chain gene; and c) a nucleotide sequence between the 3' and 5' termini according to the formula:

$$[NNK]_m$$

wherein N is independently any nucleotide, K is G or T, and n is 3 to about 24, said 3' and 5' terminal nucleotide sequences having a length of about 6 to 50 nucleotides. Also contemplated are oligonucleotides having a sequence complementary thereto.

In a preferred embodiment, the invention contemplates the above mutagenesis method that further comprises the steps of:

a) isolating the amplified CDR to form a library of mutagenized immunoglobulin light chain genes;

b) expressing the isolated library of mutagenized light chain genes in combination with one or more heavy chain genes to form a combinatorial antibody library of expressed heavy and light chain genes; and c) selecting species of the combinatorial antibody library for the ability to bind a preselected antigen. In one embodiment, the one or more immunoglobulin heavy chain genes can be provided as a library of heavy chain genes as described further herein.

In a related embodiment, the oligonucleotide used in the method can have a nucleotide sequence between the 3' and 5' termini according to the formula:

$$[MNN]_m$$

wherein N is independently any nucleotide, M is A or C, and n is 3 to about 24.

In addition, it is shown in the present invention that particular immunoglobulin light chain variable domain polypeptides are useful as a light chain partner for a large variety of heavy chains, i.e., the light chain forms functional heterodimeric antibody molecules upon association with different heavy chains, demonstrating the ability to function universally as a light chain in the presently described combinatorial libraries.

Thus, in preferred mutagenesis methods, the immunoglobulin variable domain light chain gene includes a sequence having the sequence characteristics selected from the group consisting of light chains shown in SEQ ID NOs 2 and 62 which encode the preferred universal light chain polypeptides described herein.

In a related embodiment, the invention contemplates the direct use of the universal light chain polypeptide gene without diversification by mutagenesis of its CDR domains. Specifically, the invention contemplates a method for producing a heterodimeric immunoglobulin molecule having immunoglobulin variable domain heavy and light chain polypeptides comprising the steps of:

a) combining an immunoglobulin variable domain light chain gene that includes a sequence having the sequence characteristics of a light chain selected from the group consisting of light chains shown in SEQ ID NO 2 and 62 with one or more immunoglobulin variable domain heavy chain genes to form a combinatorial immunoglobulin heavy and light chain gene library, where the combining comprising operatively linking the light chain gene with one of the heavy chain genes in a vector capable of co-expression of the heavy and light chain genes;

b) expressing the combinatorial gene library to form a combinatorial antibody library of expressed heavy and light chain polypeptides; and c) selecting species of the combinatorial antibody library for the ability to bind a preselected antigen.

Also contemplated are oligonucleotide compositions for use as PCR primers to perform the recited mutageneses.

BRIEF DESCRIPTION OF THE DRAWINGS

In the drawings forming a portion of this disclosure.

DETAILED DESCRIPTION OF THE INVENTION

A. Definitions

Figure 1:
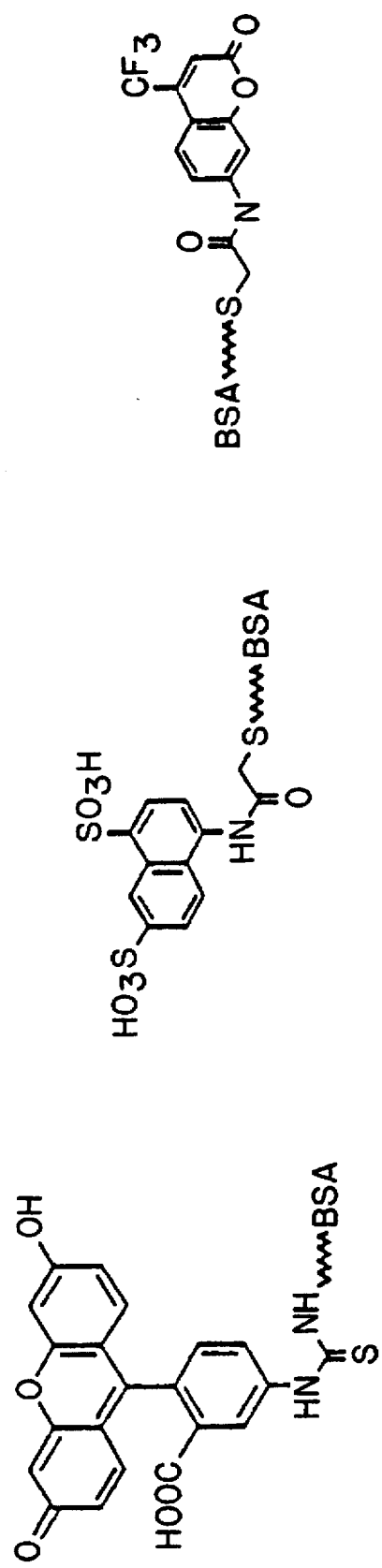
FIG. 1 illustrates the structures of hapten conjugates used for selection of the semisynthetic Fab heterodimers of this invention. Conjugate 1 is fluorescein-BSA (F1-BSA) as described in Example 5B. Conjugates 2 and 3, respectively, S-BSA and C-BSA, were prepared as described in Example 5B.

Amino Acid Residue: An amino acid formed upon chemical digestion (hydrolysis) of a polypeptide at its peptide linkages. The amino acid residues described herein are preferably in the "L" isomeric form. However, residues in the "D" isomeric form can be substituted for any L-amino acid residue, as long as the desired functional property is retained by the polypeptide. NH$_2$ refers to the free amino group present at the amino terminus of a polypeptide. COOH refers to the free carboxy group present at the carboxy terminus of a polypeptide. In keeping with standard polypeptide nomenclature (described in *J. Biol. Chem.*, 243:3552–59 (1969) and adopted at 37 CFR §1.822(b)(2)), abbreviations for amino acid residues are shown in the following Table of Correspondence:

TABLE OF CORRESPONDENCE

| SYMBOL | | |
|---|---|---|
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| A | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| Z | Glx | Glu and/or Gln |
| W | Trp | tryptophan |
| R | Arg | arginine |
| D | Asp | aspartic acid |
| N | Asn | asparagine |
| B | Asx | Asn and/or Asp |
| C | Cys | cysteine |
| X | Xaa | Unknown or other |

It should be noted that all amino acid residue sequences represented herein by formulae have a left-to-right orientation in the conventional direction of amino terminus to carboxy terminus. In addition, the phrase "amino acid residue" is broadly defined to include the amino acids listed in the Table of Correspondence and modified and unusual amino acids, such as those listed in 37 CFR 1.822(b)(4), and incorporated herein by reference. Furthermore, it should be noted that a dash at the beginning or end of an amino acid residue sequence indicates a peptide bond to a further sequence of one or more amino acid residues or a covalent bond to an amino-terminal group such as NH$_2$ or acetyl or to a carboxy-terminal group such as COOH.

Recombinant DNA (rDNA) Molecule: A DNA molecule produced by operatively linking two DNA segments. Thus, a recombinant DNA molecule is a hybrid DNA molecule comprising at least two nucleotide sequences not normally found together in nature. rDNA's not having a common biological origin, i.e., evolutionarily different, are said to be "heterologous".

Vector: A rDNA molecule capable of autonomous replication in a cell and to which a DNA segment, e.g., gene or polynucleotide, can be operatively linked so as to bring about replication of the attached segment. Vectors capable of directing the expression of genes encoding for one or more polypeptides are referred to herein as "expression vectors". Particularly important vectors allow cloning of cDNA (complementary DNA) from mRNAs produced using reverse transcriptage.

Receptor: A receptor is a molecule, such as a protein, glycoprotein and the like, that can specifically (non-randomly) bind to another molecule.

Antibody: The term antibody in its various grammatical forms is used herein to refer to immunoglobulin molecules and immunologically active portions of immunoglobulin molecules, i.e., molecules that contain an antibody combining site or paratope. Exemplary antibody molecules are intact immunoglobulin molecules, substantially intact immunoglobulin molecules and portions of an immunoglobulin molecule, including those portions known in the art as Fab, Fab', F(ab')$_2$ and F(v).

Antibody Combining Site: An antibody combining site is that structural portion of an antibody molecule comprised of a heavy and light chain variable and hypervariable regions that specifically binds (immunoreacts with) an antigen. The term immunoreact in its various forms means specific binding between an antigenic determinant-containing molecule and a molecule containing an antibody combining site such as a whole antibody molecule or a portion thereof.

Monoclonal Antibody: A monoclonal antibody in its various grammatical forms refers to a population of antibody molecules that contain only one species of antibody combining site capable of immunoreacting with a particular epitope. A monoclonal antibody thus typically displays a single binding affinity for any epitope with which it immunoreacts. A monoclonal antibody may therefore contain an antibody molecule having a plurality of antibody combining sites, each immunospecific for a different epitope, e.g., a bispecific monoclonal antibody. Although historically a monoclonal antibody was produced by immortalization of a clonally pure immunoglobulin secreting cell line, a monoclonally pure population of antibody molecules can also be prepared by the methods of the present invention.

Fusion Polypeptide: A polypeptide comprised of at least two polypeptides and a linking sequence to operatively link the two polypeptides into one continuous polypeptide. The two polypeptides linked in a fusion polypeptide are typically derived from two independent sources, and therefore a fusion polypeptide comprises two linked polypeptides not normally found linked in nature.

Upstream: In the direction opposite to the direction of DNA transcription, and therefore going from 5' to 3' on the noncodingstrand, or 3' to 5' on the mRNA.

Downstream: Further along a DNA sequence in the direction of sequence transcription or read out, that is traveling in a 3'- to 5'-direction along the noncodingstrand of the DNA or 5'- to 3'-direction along the RNA transcript.

Cistron: A sequence of nucleotides in a DNA molecule coding for an amino acid residue sequence and including upstream and downstream DNA expression control elements.

Leader Polypeptide: A short length of amino acid sequence at the amino end of a polypeptide, which carries or directs the polypeptide through the inner membrane and so ensures its eventual secretion into the periplasmic space and perhaps beyond. The leader sequence peptide is commonly removed before the polypeptide becomes active.

Reading Frame: A particular sequence of contiguous nucleotide triplets (codons) employed in translation. The reading frame depends on the location of the translation initiation codon.

B. Methods For Producing Antibody Molecules or Libraries of Antibody Molecules

1. General Rationale

The present invention utilizes a system for the simultaneous cloning and screening of preselected ligand-binding specificities from gene repertoires using a single vector system. This system provides linkage of cloning and screening methodologies and has two requirements. First, that expression of the polypeptide chains of a heterodimeric receptor in an in vitro expression host such as *E. coli* requires coexpression of the two polypeptide chains in order that a functional heterodimeric receptor can assemble to produce a receptor that binds ligand. Second, that screening of isolated members of the library for a preselected ligand-binding capacity requires a means to correlate the binding capacity of an expressed receptor molecule with a convenient means to isolate the gene that encodes the member from the library.

Linkage of expression and screening is accomplished by the combination of targeting of a fusion protein into the periplasm of a bacterial cell to allow assembly of a functional receptor, and the targeting of a fusion protein onto the coat of a filamentous phage particle during phage assembly to allow for convenient screening of the library member of interest. Periplasmic targeting is provided by the presence of a secretion signal domain in a fusion protein of this invention. Targeting to a phage particle is provided by the presence of a filamentous phage coat protein membrane anchor domain in a fusion protein of this invention.

The present invention describes in one embodiment a method for producing a library of DNA molecules, each DNA molecule comprising a cistron for expressing a fusion protein on the surface of a filamentous phage particle. The method comprises the steps of (a) forming a ligation admixture by combining in a ligation buffer (i) a repertoire of immunoglobulin variable chain polypeptide-encoding genes and (ii) a plurality of DNA expression vectors in linear form adapted to form a fusion protein expressing cistron, and (b) subjecting the admixture to ligation conditions for a time period sufficient for the repertoire of genes to become operatively linked (ligated) to the plurality of vectors to form the library.

In this embodiment, the repertoire of polypeptide encoding genes are in the form of double-stranded (ds) DNA and each member of the repertoire has cohesive termini adapted for directional ligation. In addition, the plurality of DNA expression vectors are each linear DNA molecules having upstream and downstream cohesive termini that are (a) adapted for directionally receiving the polypeptide genes in a common reading frame, and (b) operatively linked to respective upstream and downstream translatable DNA sequences. The upstream translatable DNA sequence encodes a secretion signal, preferably a pelB secretion signal, and the downstream translatable DNA sequence encodes a filamentous phage coat protein membrane anchor as described herein for a polypeptide of this invention. The translatable DNA sequences are also operatively linked to respective upstream and downstream DNA expression control sequences as defined for a DNA expression vector described herein.

The library so produced can be utilized for expression and screening of the fusion proteins encoded by the resulting library of cistrons represented in the library by the expression and screening methods described herein.

2. Production of Gene Repertoires

A gene repertoire is a collection of different genes, preferably polypeptide-encoding genes (polypeptide genes), and may be isolated from natural sources or can be generated artificially. Preferred gene repertoires are comprised of conserved genes. Particularly preferred gene repertoires comprise either or both genes that code for polypeptides that can assemble to form a functional dimeric receptor molecule.

A gene repertoire useful in practicing the present invention contains at least $10^3$, preferably at least $10^4$, more preferably at least $10^5$, and most preferably at least $10^7$ different genes. Methods for evaluating the diversity of a repertoire of genes is well known to one skilled in the art.

Preferably, the receptor will be a heterodimeric polypeptide capable of binding a ligand, such as an antibody molecule or immunologically active portion thereof, coded for by one of the members of a family (repertoire) of conserved genes, i.e., genes containing a conserved nucleotide sequence of at least about 10 nucleotides in length.

A gene can be identified as belonging to a repertoire of conserved genes using several methods. For example, an isolated gene may be used as a hybridization probe under low stringency conditions to detect other members of the repertoire of conserved genes present in genomic DNA using the methods described by Southern, *J. Mol. Biol.*, 98:503 (1975). If the gene used as a hybridization probe hybridizes to multiple restriction endonuclease fragments of the genome, that gene is a member of a repertoire of conserved genes.

The present invention relates generally to methods for producing novel antibody molecules by the preparation of diverse libraries of antibodies, and subsequent screening of the libraries for desirable binding specificities. The method involves the preparation of libraries of heterodimeric immunoglobulin molecules in the form of phagemid libraries using degenerate oligonucleotides and primer extension reactions to incorporate the degeneracies into the CDR regions of the immunoglobulin variable heavy and light chain variable domains, and display of the mutagenized polypeptides on the surface of the phagemid. Thereafter, the display protein is screened for the ability to bind to a preselected antigen.

Furthermore, the libraries of heavy and light chain immunoglobulin-coding genes can be crossed to form random pairings of species of heavy and light chains, yielding higher numbers of unique heterodimers. Such crosses can be conducted in a variety of ways, as described further herein, including (1) crossing a single heavy chain to a library of light chains, (2) crossing a single light chain to a library of heavy chains, (3) crossing a randomized light or heavy chain against a single heavy or light chain, respectively, (4) crossing a randomized light or heavy chain against a heavy or light chain library, respectively, and (5) crossing a randomized light or heavy chain against a randomized heavy or light chain, respectively. Other permutations are also apparent.

By randomized is meant generally to connote the preparation of a library of light (or heavy) chain genes by mutagenesis of one or more CDR regions in the variable domain of a preselected light or heavy chain, as described further herein.

One particularly preferred permutation of the above methods to produce an antibody repertoire is by the use of randomized light chain genes crossed with a heavy chain library, and particularly crossed with a randomized heavy chain library. Another particularly preferred embodiment is the use of a "universal light chain" selected from the group consisting of light chains shown in SEQ ID NOs 2 and 62 as described further herein as the single light chain in the cross with a heavy chain library. A preferred related embodiment is the use of a randomized universal light chain against a heavy chain or heavy chain library. Other preferred methods are also described herein.

3. Phagemid Display Proteins

The display of the heterodimeric immunoglobulin molecule as a display protein on a phagemid can be accomplished on any of the surface proteins of the filamentous phage particle, although particularly preferred are display proteins comprising gene III or gene VIII protein, as described herein. The use of gene III or gene VIII protein as a display protein on filamentous phage has been extensively described elsewhere herein.

Particularly preferred display proteins are fusions involving the use of the phage particle membrane anchor derived from gene III or gene VIII fused to an immunoglobulin heavy or light chain as described herein. In this embodiment, a polypeptide containing at least one variable domain CDR of an immunoglobulin heavy or light chain is fused to the membrane anchor domain of the phage's gene III or gene VIII protein. Preferably, a complete variable domain is fused, including all the CDR's When using an immunoglobulin heavy or light chain variable region, the fusion protein can include one or more of the complementarity determining regions, CDR1, CDR2 or CDR3. Using the Kabat immunoglobulin amino acid residue sequence position numbering system, the light chain CDR's are as follows: CDR1 (residues 23–35), CDR2 (residues 49–57), and CDR3 (residues 88–98); and the heavy chain CDR's are as follows: CDR1 (residues 30–36), CDR2 (residues 49–66), and CDR3 (residues 94–103). See, Kabat et al., "Sequences of Proteins of Immunological Interest", 5th ed., NIH, (1991).

When mutagenizing a CDR of an immunoglobulin fusion display protein, some, most or all of the CDR can be removed and substituted by the newly incorporated sequences introduced by mutagenesis. CDRs are very accommodating to variably sized inserts without disrupting the ability of the immunoglobulin to assemble and display the newly randomized and selected amino acid residue sequence.

In one embodiment, a phage display protein can be engineered to contain multiple binding sites. For example, using the heavy chain immunoglobulin as exemplary, binding sites can be created separately by the methods of this invention into one or more of the CDRs, designated CDR1, CDR2 and CDR3. Additionally, one can introduce binding sites into a heavy chain CDR and a light chain CDR, into multiple heavy and light chain CDRs, and the like combinations.

In another embodiment, the phage display protein is engineered to include stabilization features in addition to the stabilization provided by the native structure of the display protein. To that end, cysteine residues can be coded for by the oligonucleotide, such that disulfide bridges can be formed. The placement of the cysteine residues can be varied, such that a loop structure of from about 5 to 20 amino acid residues is formed.

A preferred phagemid display protein utilizes an filamentous phage anchor fused to an immunoglobulin heavy chain variable domain polypeptide, and the light chain associates (assembles) with the heavy chain during expression to form the displayed heterodimeric receptor, as described further herein.

4. Oligonucleotides

The preparation of a heterodimeric immunoglobulin molecule according to the present invention involves the use of synthetic oligonucleotides designed to introduce random mutations into a preselected CDR regions of the variable domain of the heavy or light chain. Furthermore, the oligonucleotide strategy described herein has particular advantages in creating in a single reaction an extremely large population of different randomized binding sites by the use of degenerate oligonucleotides.

The mutagenizing oligonucleotide randomizes the gene coding the amino acid residue sequence of the immunoglobulin CDR, and the subsequent screening of the expressed phagemid display protein for preselected binding specificities is conducted as described herein and further in the Examples.

Several oligonucleotide designs were utilized to form a binding site of varying lengths comprising a CDR. To that end, a series of 4, 5, 6, 8, 10 or 16 consecutive amino acid residues were randomized in the CDR region of the immunoglobulin variable domain by a degenerate oligonucleotide.

The general structure of an oligonucleotide for use in the present methods has the general formula ANB, where A and B define regions of homology to regions of the immunoglobulin polypeptide gene which flank the CDR region in which mutagenesis is to be introduced and N defines the region of degeneracy in which variable amino acid residues are introduced by presenting all possible combinations of nucleotide triplets using the four bases A, T, G and C.

The number of nucleotides for each region (A, B, or N) can vary widely, but N must be in triplets so as to preserve the reading frame of the display protein. Typically, regions A and B are of sufficient length to confer hybridization specificity with the template during the primer extension reaction. Thus, regions A and B are typically each at least 6 nucleotides, and preferably each at least 9 nucleotides in length, although they can be up to about 50 nucleotides in length. The N's are typically of a widely variable length coding typically from 3 to 24 amino acid residues in length.

Where the display protein is an immunoglobulin, the homologies in regions A and B are directed to the immunoglobulin framework regions (FR) that flank the CDR into which the binding site is to be inserted.

Thus, in one embodiment, the invention contemplates an oligonucleotide useful as a primer for inducing mutagenesis in a CDR of an immunoglobulin heavy or light chain gene. The oligonucleotide has 5' and 3' termini and comprises:

i) a nucleotide sequence of about 6 to 50 nucleotides in length at the 3' termini capable of hybridizing to a first framework region of the immunoglobulin gene;

ii) a nucleotide sequence of about 6 to 50 nucleotides in length at the 5' termini capable of hybridizing to a second framework region of the immunoglobulin gene; and iii) a nucleotide sequence between said 5' and 3' termini according to the formula:

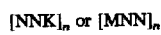

where n is a whole integer from 3 to 24, N is independently any nucleotide, K is G or T, M is A or C, and wherein said 5' and 3' terminal nucleotide sequences have a length of about 6 to 50 nucleotides in length, or an oligonucleotide having a sequence complementary thereto. Preferably, n is 4, 5, 6, 8, 10 or 16.

The choice of framework regions depends on the CDR into which the binding site is to be inserted. Thus, for example, for an insertion into CDR3, the 3' and 5' regions of the oligonucleotides are selected as to be complementary in nucleotide sequence to the coding strand defining FR4 and FR3 that flank CDR3, respectively, where the oligonucleotide is to be complementary to the noncoding (anti-sense) strand of the template DNA.

Furthermore, the framework region sequence varies depending upon whether an immunoglobulin heavy or light chain CDR region is being mutagenized by the present methods.

A preferred and exemplary CDR for insertion of a binding site is the CDR3 of immunoglobulin heavy or light chain. Exemplary immunoglobulin heavy and light chain polypeptides are expressed by the phagemid vector pC3AP313, described herein.

Preferred are human immunoglobulin heterodimeric molecules, and therefore, in preferred embodiments, the immunoglobulin to be mutagenized, and the oligonucleotide complementary thereto, is of human derivation.

Oligonucleotides used in the present methods that are particularly preferred for producing mutagenized heavy or light chain CDR's are described in the Examples.

As described herein, the strategy for mutagenesis by polymerase chain reaction amplification can vary widely. Two different strategies are described in detail, differing in the oligonucleotide which introduces the degenerate nucleotides. Thus, degenerate PCR primers can be designed to be coding or non-coding depending upon whether they are the upstream or downstream PCR primer. A primer can also be designed to be complementary to those described herein and be functionally equivalent.

Similarly, the framework sequences can vary in length while maintaining the degree of mutation to the CDR, as described in the example of oligonucleotide primer pools KV6R and k10, described herein. Thus, an oligonucleotide can be comprised of varying 5' and 3' termini, and a varying amount of degenerate triplet nucleotides as described herein.

Preferred oligonucleotides for mutagenizing light chain are described in the Examples, and include the oligonucleotide primer pools KV4R, k8, KV5R, k9, KV6R, k10, KV10R, p313K380Vb, p313K3100Vb and p313K3160Vb. Other oligonucleotides can be utilized as is appreciated by one skilled in the art.

Oligonucleotides for use in the present invention can be synthesized by a variety of chemistries as is well known. An excellent review is "Oligonucleotide Synthesis: A Practical Approach", ed. M. J. Gait, JRL Press, New York, N.Y. (1990). Suitable synthetic methods include, for example, the phosphotriester or phosphodiester methods see Narang et al., *Meth. Enzymolo*, 68:90, (1979); U.S. Pat. No. 4,356,270; and Brown et al., *Meth. Enzymol.*, 68:109, (1979). Purification of synthesized oligonucleotides for use in primer extension and PCR reactions is well known. See, example Ausubel et al., "Current Protocols in Molecular Biology", John Wiley & Sons, New York, (1987). Oligonucleotides for use in the present invention are commercially synthesized by Operon Technologies, Alameda, Calif.

5. Primer Extension Reactions

The terms "polynucleotide" and "oligonucleotide" as used herein in reference to primers, probes and nucleic acid fragments or segments to be synthesized by primer extension is defined as a molecule comprised of two or more deoxyribonucleotides or ribonucleotides, preferably more than three. Its exact size will depend on many factors, which in turn depends on the ultimate conditions of use.

The term "primer" as used herein refers to a polynucleotide whether purified from a nucleic acid restriction digestion reaction or produced synthetically, which is capable of acting as a point of initiation of nucleic acid synthesis when placed under conditions in which synthesis of a primer extension product which is complementary to a nucleic acid strand is induced, i.e., in the presence of nucleotides and an agent for polymerization such as DNA polymerase, reverse transcriptase and the like, and at a suitable temperature and Ph. The primer is preferably single stranded for maximum efficiency, but may alternatively be in double stranded form.

If double stranded, the primer is first treated to separate it from its complementary strand before being used to prepare extension products. Preferably, the primer is a polydeoxyribonucleotide. The primer must be sufficiently long to prime the synthesis of extension products in the presence of the agents for polymerization. The exact lengths of the primers will depend on many factors, including temperature and the source of primer. For example, depending on the complexity of the target sequence, a polynucleotide primer typically contains 15 to 25 or more nucleotides, although it can contain fewer nucleotides. Short primer molecules generally require cooler temperatures to form sufficiently stable hybrid complexes with template.

The primers used herein are selected to be "substantially" complementary to the different strands of each specific sequence to be synthesized or amplified. This means that the primer must be sufficiently complementary to non-randomly hybridize with its respective template strand. Therefore, the primer sequence may or may not reflect the exact sequence of the template. For example, a non-complementary nucleotide fragment can be attached to the 5' end of the primer, with the remainder of the primer sequence being substantially complementary to the strand. Such non-complementary fragments typically code for an endonuclease restriction site. Alternatively, non-complementary bases or longer sequences can be interspersed into the primer, provided the primer sequence has sufficient complementarily with the sequence of the strand to be synthesized or amplified to non-randomly hybridize therewith and thereby form an extension product under polynucleotide synthesizing conditions.

Primers of the present invention may also contain a DNA-dependent RNA polymerase promoter sequence or its complement. See for example, Krieg et al., *Nucl. Acids Res.*, 12:7057–70 (1984); Studier et al., *J. Mol. Biol.*, 189:113–130 (1986); and *Molecular Cloning: A Laboratory Manual, Second Edition*, Sambrook et al., eds., Cold Spring Harbor, N.Y. (1989).

When a primer containing a DNA-dependent RNA polymerase promoter is used the primer is hybridized to the polynucleotide strand to be amplified and the second polynucleotide strand of the DNA-dependent RNA polymerase promoter is completed using an inducing agent such as *E. coli* DNA polymerase I, or the Klenow fragment of *E. coli* DNA polymerase. The starting polynucleotide is amplified by alternating between the production of an RNA polynucleotide and DNA polynucleotide.

Primers may also contain a template sequence or replication initiation site for a RNA-directed RNA polymerase. Typical RNA-directed RNA polymerase include the QB replicase described by Lizardi et al., *Biotechnology*, 6:1197–1202 (1988). RNA-directed polymerases produce large numbers of RNA strands from a small number of template RNA strands that contain a template sequence or replication initiation site. These polymerases typically give a one million-fold amplification of the template strand as has been described by Kramer et al., *J. Mol. Biol.*, 89:719–736 (1974).

The choice of a primer's nucleotide sequence depends on factors such as the distance on the nucleic acid from the region of the display protein gene into which a binding site is being introduced, its hybridization site on the nucleic acid relative to any second primer to be used, and the like.

The PCR reaction is performed using any suitable method. Generally it occurs in a buffered aqueous solution, i.e., a PCR buffer, preferably at a Ph of 7–9, most preferably about 8. Preferably, a molar excess of the primer is admixed to the buffer containing the template strand. A large molar excess of about $10^4$:1 of primer to template is preferred to improve the efficiency of the process.

The PCR buffer also contains the deoxyribonucleotide triphosphates dATP, dCTP, dGTP, and dTTP and a polymerase, typically thermostable, all in adequate amounts for primer extension (polynucleotide synthesis) reaction. The resulting solution (PCR admixture) is heated to about 90 degrees Celsius (90C)–100C for about 1 to 10 minutes, preferably from 1 to 4 minutes. After this heating period the solution is allowed to cool to 54C, which is preferable for primer hybridization. The synthesis reaction may occur at from room temperature up to a temperature above which the polymerase (inducing agent) no longer functions efficiently. Thus, for example, if DNA polymerase is used as inducing agent, the temperature is generally no greater than about 40C. An exemplary PCR buffer comprises the following: 50 Mm KCl; 10 Mm Tris-Hcl; Ph 8.3; 1.5 Mm $MgCl_2$; 0.001% (wt/vol) gelatin, 200 micromolar (uM) DATP; 200 uM DTTP; 200 uM DCTP; 200 uM DGTP; and 2.5 units *Thermus aquaticus* DNA polymerase I (U.S. Pat. No. 4,889,818) per 100 microliters of buffer. Exemplary PCR amplifications are performed using the buffer system as described in the Examples.

The inducing agent may be any compound or system which will function to accomplish the synthesis of primer extension products, including enzymes. Suitable enzymes for this purpose include, for example, *E. coli* DNA polymerase I, Klenow fragment of *E. coli* DNA polymerase I, T4 DNA polymerase, other available DNA polymerases, reverse transcriptase, and other enzymes, including heat-stable enzymes, which will facilitate combination of the nucleotides in the proper manner to form the primer extension products which are complementary to each nucleic acid strand. Generally, the synthesis will be initiated at the 3' end of each primer and proceed in the 5' direction along the template strand, until synthesis terminates, producing molecules of different lengths. There may be inducing agents, however, which initiate synthesis at the 5' end and proceed in the above direction, using the same process as described herein.

The inducing agent also may be a compound or system which will function to accomplish the synthesis of RNA primer extension products, including enzymes. In preferred embodiments, the inducing agent may be a DNA-dependent RNA polymerase such as T7 RNA polymerase, T3 RNA polymerase or SP6 RNA polymerase. These polymerases produce a complementary RNA polynucleotide. The high turn over rate of the RNA polymerase amplifies the starting polynucleotide as has been described by Chamberlin et al., *The Enzymes*, ed. P. Boyer, PP. 87–108, Academic Press, New York (1982). Another advantage of T7 RNA polymerase is that mutations can be introduced into the polynucleotide synthesis by replacing a portion of CDNA with one or more mutagenic oligodeoxynucleotides (polynucleotides) and transcribing the partially-mismatched template directly as has been previously described by Joyce et al., *Nuc. Acids Res.*, 17:711–722 (1989). Amplification systems based on transcription have been described by Gingeras et al., in *PCR Protocols, A Guide to Methods and Applications*, pp 245–252, Academic Press, Inc., San Diego, Calif. (1990) .

If the inducing agent is a DNA-dependent RNA polymerase and therefore incorporates ribonucleotide triphosphates, sufficient amounts of ATP, CTP, GTP and UTP are admixed to the primer extension reaction admixture and the resulting solution is treated as described above.

The newly synthesized strand and its complementary nucleic acid strand form a double-stranded molecule which can be used in the succeeding steps of the process, as is known for PCR.

PCR is typically carried out by thermocycling i.e., repeatedly increasing and decreasing the temperature of a PCR reaction admixture within a temperature range whose lower limit is about 10C to about 40C and whose upper limit is about 90C to about 100C. The increasing and decreasing can be continuous, but is preferably phasic with time periods of relative temperature stability at each of temperatures favoring polynucleotide synthesis, denaturation and hybridization.

PCR amplification methods are described in detail in U.S. Pat. Nos. 4,683,192, 4,683,202, 4,800,159, and 4,965,188, and at least in several texts including "PCR Technology: Principles and Applications for DNA Amplification", H. Erlich, ed., Stockton Press, New York (1989); and "PCR Protocols: A Guide to Methods and Applications", Innis et al., eds., Academic Press, San Diego, Calif. (1990); the teachings of which are hereby incorporated by reference.

PCR can be conducted to ligate two different PCR reaction products in a method referred to as overlapping PCR or crossover PCR. This method is used to connect heavy and light chain PCR reaction products, and is described herein. In the overlapping PCR method, it is convenient to introduce the mutagenesis of a CDR by designing either the 3' primer or the 5' primer as the degenerate oligonucleotide in the primer pair. Both methods are described in the Examples.

Additional preferred PCR reactions using the oligonucleotides and methods of this invention are described in the Examples.

6. Phage Display Vectors

Random mutagenesis of CDRs in a variable (V) region and screening methods such as is described by Barbas et al, *Proc. Natl. Acad. Sci., USA*, 89:4457–4461, (1992) are used for preparing antibody libraries that contain diverse binding site specificities with the improvements described herein.

The methods of the present invention for preparing antibody molecules involve the use of phage display vectors for their particular advantage of providing a means to screen a very large population of expressed display proteins and thereby locate one or more specific clones that code for a desired binding reactivity.

The use of phage display vectors derives from the previously described use of combinatorial libraries of antibody molecules based on phagemids. The combinatorial library production and manipulation methods have been extensively described in the literature, and will not be reviewed in detail herein, except for those features required to make and use unique embodiments of the present invention. However, the methods generally involve the use of a filamentous phage (phagemid) surface expression vector system for cloning and expressing antibody species of the library.

Various phagemid cloning systems for producing combinatorial libraries have been described by others. See for example the preparation of combinatorial antibody libraries on phagemids as described by Kang et al., *Proc. Natl. Acad. Sci., USA*, 88:4363–4366 (1991); Barbas et al., *Proc. Natl. Acad. Sci., USA*, 88:7978–7982 (1991); Zebedee et al., *Proc. Natl. Acad. Sci., USA*, 89:3175–3179 (1992); Kang et al., *Proc. Natl. Acad. Sci., USA*, 88:11120–11123 (1991); Barbas et al., *Proc. Natl. Acad. Sci., USA*, 89:4457–4461 (1992); and Gram et al., *Proc. Natl. Acad. Sci., USA*, 89:3576–3580 (1992), the disclosures of which are hereby incorporated by reference.

a. Phage Display Vector Structure

A preferred phagemid vector of the present invention is a recombinant DNA (RDNA) molecule containing a nucleotide sequence that codes for and is capable of expressing a fusion polypeptide containing, in the direction of amino- to carboxy-terminus, (1) a prokaryotic secretion signal domain, (2) a heterologous polypeptide defining an immunoglobulin heavy or light chain variable region, and (3) a filamentous phage membrane anchor domain. The vector includes DNA expression control sequences for expressing the fusion polypeptide, preferably prokaryotic control sequences.

The filamentous phage membrane anchor is preferably a domain of the cpiii or cpviii coat protein capable of associating with the matrix of a filamentous phage particle, thereby incorporating the fusion polypeptide onto the phage surface.

Preferred membrane anchors for the vector are obtainable from filamentous phage M13, f1, fd, and equivalent filamentous phage. Preferred membrane anchor domains are found in the coat proteins encoded by gene III and gene VIII. The membrane anchor domain of a filamentous phage coat protein is a portion of the carboxy terminal region of the coat protein and includes a region of hydrophobic amino acid residues for spanning a lipid bilayer membrane, and a region of charged amino acid residues normally found at the cytoplasmic face of the membrane and extending away from the membrane.

In the phage f1, gene VIII coat protein's membrane spanning region comprises residue Trp-26 through Lys-40, and the cytoplasmic region comprises the carboxy-terminal 11 residues from 41 to 52 (Ohkawa et al., *J. Biol. Chem.*, 256:9951–9958, 1981). An exemplary membrane anchor would consist of residues 26 to 40 of cpviii. Thus, the amino acid residue sequence of a preferred membrane anchor domain is derived from the M13 filamentous phage gene VIII coat protein (also designated cpviii or CP 8). Gene VIII coat protein is present on a mature filamentous phage over the majority of the phage particle with typically about 2500 to 3000 copies of the coat protein.

In addition, the amino acid residue sequence of another preferred membrane anchor domain is derived from the M13 filamentous phage gene III coat protein (also designated cpiii). Gene III coat protein is present on a mature filamentous phage at one end of the phage particle with typically about 4 to 6 copies of the coat protein.

For detailed descriptions of the structure of filamentous phage particles, their coat proteins and particle assembly, see the reviews by Rached et al., *Microbiol. Rev.*, 50:401–427 (1986); and Model et al., in "The Bacteriophages: Vol. 2", R. Calendar, ed. Plenum Publishing Co., pp. 375–456 (1988).

The secretion signal is a leader peptide domain of a protein that targets the protein to the periplasmic membrane of gram negative bacteria. A preferred secretion signal is a pelB secretion signal. The predicted amino acid residue sequences of the secretion signal domain from two pelB gene product variants from *Erwinia carotova* are described in Lei et al., *Nature*, 331:543–546 (1988).

The leader sequence of the pelB protein has previously been used as a secretion signal for fusion proteins (Better et al., *Science*, 240:1041–1043 (1988); Sastry et al., *Proc. Natl. Acad. Sci., USA*, 86:5728–5732 (1989); and Mullinax et al., *Proc. Natl. Acad. Sci., USA*, 87:8095–8099 (1990)). Amino acid residue sequences for other secretion signal polypeptide domains from *E. coli* useful in this invention as described in Oliver, *Escherichia coli* and *Salmonella Typhimurium*, Neidhard, F. C. (ed.), American Society for Microbiology, Washington, D.C., 1:56–69 (1987).

DNA expression control sequences comprise a set of DNA expression signals for expressing a structural gene product and include both 5' and 3' elements, as is well known, operatively linked to the cistron such that the cistron is able to express a structural gene product. The 5' control sequences define a promoter for initiating transcription and a ribosome binding site operatively linked at the 5' terminus of the upstream translatable DNA sequence.

The 3' control sequences define at least one termination (stop) codon in frame with and operatively linked to the heterologous fusion polypeptide.

In preferred embodiments, the vector used in this invention includes a prokaryotic origin of replication or replicon, i.e., a DNA sequence having the ability to direct autonomous replication and maintenance of the recombinant DNA molecule extra-chromosomally in a prokaryotic host cell, such as a bacterial host cell, transformed therewith. Such origins of replication are well known in the art. Preferred origins of replication are those that are efficient in the host organism. A preferred host cell is *E. coli*. A preferred strain of *E. coli* is the supE strain as an amber stop codon is translated as glutamine (Q). For use of a vector in *E. coli*, a preferred origin of replication is ColE1 found in pBR322 and a variety of other common plasmids. Also preferred is the p15A origin of replication found on pACYC and its derivatives. The ColE1 and p15A replicon have been extensively utilized in molecular biology, are available on a variety of plasmids and are described at least by Sambrook et al., in "Molecular Cloning: a Laboratory Manual", 2nd edition, Cold Spring Harbor Laboratory Press, New York (1989).

The ColE1 and p15A replicons are particularly preferred for use in one embodiment of the present invention where two "binary" plasmids are utilized because they each have the ability to direct the replication of plasmid in *E. coli* while the other replicon is present in a second plasmid in the same *E. coli* cell. In other words, ColE1 and p15A are non-interfering replicons that allow the maintenance of two plasmids in the same host (see, for example, Sambrook et al., supra, at pages 1.3–1.4). This feature is particularly important when using binary vectors because a single host cell permissive for phage replication must support the independent and simultaneous replication of two separate vectors, for example when a first vector expresses a heavy chain polypeptide and a second vector expresses a light chain polypeptide, and the admixture of libraries of heavy and light chain gene is desired to combine all possible combinations of heavy and light chain.

In addition, those embodiments that include a prokaryotic replicon can also include a gene whose expression confers a selective advantage, such as drug resistance, to a bacterial host transformed therewith. Typical bacterial drug resistance genes are those that confer resistance to ampicillin, tetracycline, neomycin/kanamycin or chloramphenicol. Vectors typically also contain convenient restriction sites for insertion of translatable DNA sequences. Exemplary vectors are the plasmids pUC8, pUC9, PBR322, and pBR329 available from BioRad Laboratories, (Richmond, Calif.) and pPL and pKK223 available from Pharmacia, (Piscataway, N.J.).

As used herein, the term "vector" refers to a nucleic acid molecule capable of transporting between different genetic environments another nucleic acid to which it has been operatively linked. Preferred vectors are those capable of autonomous replication and expression of structural gene products present in the DNA segments to which they are operatively linked. Vectors, therefore, preferably contain the replicons and selectable markers described earlier.

As used herein with regard to DNA sequences or segments, the phrase "operatively linked" means the sequences or segments have been covalently joined, preferably by conventional phosphodiester bonds, into one strand of DNA, whether in single or double stranded form, in a manner such that the sequences are able to function in the vector, ie., to be expressed. The choice of vector to which a transcription unit or a cassette of this invention is operatively linked depends directly, as is well known in the art, on the functional properties desired, e.g., vector replication and protein expression, and the host cell to be transformed, these being limitations inherent in the art of constructing recombinant DNA molecules.

In a preferred embodiment, the vector is capable of co-expression of two cistrons contained therein, such as a heavy chain gene and a light chain gene. Co-expression has been accomplished in a variety of systems and therefore need not be limited to any particular design, so long as sufficient relative amounts of the two gene products are produced to allow assembly and expression of functional heterodimer. Preferred vectors capable of co-expression are described herein.

In a preferred embodiment, a DNA expression vector is designed for convenient manipulation in the form of a filamentous phage particle encapsulating a genome according to the teachings of the present invention. In this embodiment, a DNA expression vector further contains a nucleotide sequence that defines a filamentous phage origin of replication such that the vector, upon presentation of the appropriate genetic complementation, can replicate as a filamentous phage in single stranded replicative form and be packaged into filamentous phage particles. This feature provides the ability of the DNA expression vector to be packaged into phage particles for subsequent segregation of the particle, and vector contained therein, away from other particles that comprise a population of phage particles.

A filamentous phage origin of replication is a region of the phage genome, as is well known, that defines sites for initiation of replication, termination of replication and packaging of the replicative form produced by replication (see for example, Rasched et al., *Microbiol. Rev.*, 50:401–427, 1986; and Horiuchi, *J. Mol. Biol.*, 188:215–223, 1986). A preferred filamentous phage origin of replication for use in the present invention is an M13, f1 or fd phage origin of replication (Short et al., *Nucl. Acids Res.*, 16:7583–7600, 1988).

A preferred DNA expression vector for cloning, mutagenesis and expressing a phagemid display protein of this invention is the dicistronic phagemid expression vector pC3AP313 described herein. pC3AP313 is capable of co-expressing both the phagemid display protein containing a heavy chain fusion and the light chain.

It is to be understood that, due to the genetic code and its attendant redundancies, numerous polynucleotide sequences can be designed that encode a contemplated heavy or light chain immunoglobulin variable region amino acid residue sequence. Thus, the invention contemplates such alternate polynucleotide sequences incorporating the features of the redundancy of the genetic code, and sequences complementary thereto.

Insofar as the expression vector for producing a human monoclonal antibody of this invention is carried in a host cell compatible with expression of the antibody, the invention contemplates a host cell containing a vector or polynucleotide of this invention. A preferred host cell is *E. coli*, as described herein.

The preferred phagemid expression vector in the form of plasmid that produces a phagemid display protein of this invention was deposited pursuant to Budapest Treaty requirements with the American Type Culture Collection (ATCC), Rockville, Md. The phagemid expression vector pC3AP313 has the respective ATCC Accession Number 75408, and includes a preferred immunoglobulin light chain variable domain polypeptide encoding gene.

b. Use of Phagemid Display Vectors to Produce Antibody Libraries

A phagemid vector for use herein is a recombinant DNA (RDNA) molecule containing a nucleotide sequence that codes for and is capable of expressing an antibody-derived heterodimeric protein on the surface of the phagemid in the form of a phagemid display protein. An exemplary and preferred phagemid vector is the plasmid pC3AP313 described in the Examples.

The method for producing a heterodimeric immunoglobulin molecule generally involves (1) introducing a heavy or light chain V region-coding gene of interest into the phagemid display vector; (2) introducing a randomized binding site into the phagemid display protein vector by primer extension with an oligonucleotide containing regions of homology to a CDR of the antibody V region gene and containing regions of degeneracy for producing randomized coding sequences as described herein, to form a large population of display vectors each capable of expressing different putative binding sites displayed on a phagemid surface display protein, (3) expressing the display protein and binding site on the surface of a filamentous phage particle, and (3) isolating (screening) the surface-expressed phage particle using affinity techniques such as panning of phage particles against a preselected antigen, thereby isolating one or more species of phagemid containing a display protein containing a binding site that binds a preselected antigen.

As a further characterization of the produced antibody binding site, the nucleotide and corresponding amino acid residue sequence of the gene coding the randomized CDR is determined by nucleic acid sequencing. The primary amino acid residue sequence information provides essential information regarding the binding site's reactivity.

An exemplary preparation of an antibody binding site in the CDR3 of the variable domains of the heavy and light chains of an immunoglobulin heterodimer is described in the Examples. The isolation of a particular vector capable of expressing an antibody binding site of interest involves the introduction of the dicistronic expression vector able to express the phagemid display protein into a host cell permissive for expression of filamentous phage genes and the assembly of phage particles. Typically, the host is *E. coli*. Thereafter, a helper phage genome is introduced into the host cell containing the phagemid expression vector to provide the genetic complementation necessary to allow phage particles to be assembled.

The resulting host cell is cultured to allow the introduced phage genes and display protein genes to be expressed, and for phage particles to be assembled and shed from the host cell. The shed phage particles are then harvested (collected) from the host cell culture media and screened for desirable antibody binding properties. Typically, the harvested particles are "panned" for binding with a preselected antigen. The strongly binding particles are then collected, and individual species of particles are clonally isolated and further screened for binding to the antigen. Phage which produce a binding site of desired antigen binding specificity are selected.

A number of different permutations for manipulation of a phagemid display vector for practicing the present invention are described herein, but the invention need not be limited.

The invention describes, in one embodiment, a method for producing an antibody combining site in a polypeptide of either the heavy or light chain of a heterodimer that comprises inducing mutagenesis in a complementarity determining region of an immunoglobulin heavy or light chain gene which comprises amplifying a CDR portion of the immunoglobulin gene by PCR using a PCR primer oligonucleotide of this invention to introduce random mutagenesis into the CDR portion.

7. Universal Light Chain

The present invention also describes the discovery of immunoglobulin light chains which have the ability to complex into a functional heterodimer with any of a variety of heavy chains, and therefore are referred to as universal light chains to connote their ability to be used with a variety of heavy chains.

Of particular utility is the ease and diversity in producing large antibody repertoires using a universal light chain. In one approach, a universal light chain is crossed with a heavy chain library, such as a randomized heavy chain. In a particular embodiment, a heavy chain of preferred specificity is randomized by CDR mutagenesis, and the resulting heavy chain library is crossed with a universal light chain to form an antibody repertoire which is then screened for desirable binding affinities. This approach provides optimization of a known heavy chain to produce improved binding specificity. The use of a universal light chain increases the number of combinations which yield functional heterodimeric antibody molecules.

In another embodiment, the invention contemplates the use of universal light chain as a framework for mutagenesis to yield a library of modified universal light chain genes. This light chain library can be used to optimize a known heavy chain, or can be crossed with a heavy chain library, as described herein.

Universal light chain is an immunoglobulin light chain polypeptide that includes at least one CDR and has the capacity to complex with a substantial variety of heavy chains in a heavy chain library. By "substantial variety of heavy chains in a heavy chain library" is meant that the universal light chain complexes with at least 0.1% of the heavy chain species in a heavy chain library, preferably with at least 1%, and more preferably with at least 10% of the heavy chain species in a heavy chain library.

A preferred universal light chain has the sequence characteristics of the light chain amino acid residue sequence shown in SEQ ID NO 2 or the sequence encoded by the light chain gene in plasmid pC3AP313 deposited with the ATCC as Accession No. ATCC 75408. A preferred universal light chain may also have the sequence characteristics of the light chain amino acid residue sequence shown in SEQ ID NO 62 or the sequence encoded by the light chain gene in plasmid p6F described in Example 8B1. By sequence characteristics is meant that the expressed light chain protein functions in a similar manner as the light chains shown in SEQ ID NOs 2 and 62. Similarity is indicated where the expressed light chain gene functionally associates with the same, or substantially the same, heavy chain genes to produce a heterodimer which immunocomplexes antigen with the same or substantially same immunoaffinity as a heterodimer formed with the light chains shown in SEQ ID NOs 2 and 62. Preferably, a universal light chain includes an amino acid residue sequence shown in SEQ ID NOs 2 and 62.

Thus, in one embodiment, the invention contemplates the preparation of a heterodimeric immunoglobulin (antibody) molecule having variable domain heavy and light chain polypeptides using a universal light chain gene in a cross with a library of heavy chain genes, followed by expression and screening according to the present invention. The method comprises the steps of:

a) combining an immunoglobulin variable domain light chain gene that includes a sequence having the sequence characteristics of the light chain shown in SEQ ID NO 2 or 62 with one or more immunoglobulin variable domain heavy chain genes to form a combinatorial immunoglobulin heavy and light chain gene library, said combining comprising operatively linking said light chain gene with one of said heavy chain genes in a vector capable of co-expression of said heavy and light chain genes;

b) expressing the combinatorial gene library to form a combinatorial antibody library of expressed heavy and light chain polypeptides; and c) selecting species of said combinatorial antibody library for the ability to bind a preselected antigen.

In preferred embodiments, the heavy chain library used in the foregoing method is a randomized heavy chain library with a mutagenized CDR domain. In preferred embodiments, the immunoglobulin light chain gene used in the foregoing method has the sequence characteristics of the light chain gene in SEQ ID NO 2 or 62.

In another embodiment, the invention contemplates the use of universal light chain in the mutagenesis methods to form a light chain library according to the present invention. Mutagenesis of light chain in this manner can be conducted in a variety of ways, such as is described in detail in the Examples.

EXAMPLES

The following examples relating to this invention are illustrative and should not, of course, be construed as specifically limiting the invention. Moreover, such variations of the invention, now known or later developed, which would be within the purview of one skilled in the art are to be considered to fall within the scope of the present invention hereinafter claimed.

1. Production of Phagemid-Displayed Fab Heavy and Light Chain Heterodimers that Bind to Synthetic Hapten Conjugates In practicing this invention to obtain expression of Fab antibodies having anti-hapten binding sites, the Fabs of which are expressed on a phage surface, the heavy (Fd consisting of $V_H$ and $C_H1$) and light (kappa) chains ($V_L$, $C_L$) of antibodies were first targeted to the periplasm of E. coli for the assembly of heterodimeric Fab molecules. In this system, the first cistron encoded a periplasmic secretion signal (pelB leader) operatively linked to the fusion protein, Fd-cpiii. The second cistron encoded a second pelB leader operatively linked to a kappa light chain. The presence of the pelB leader facilitated the coordinated but separate secretion of both the fusion protein containing the native as well as semisynthetic binding site and light chain from the bacterial cytoplasm into the periplasmic space.

In this process, each chain was delivered to the periplasmic space by the pelB leader sequence, which was subsequently cleaved. The heavy chain was anchored in the membrane by the cpiii membrane anchor domain while the light chain was secreted into the periplasm. Fab molecules were formed from the binding of the heavy chain with the soluble light chains. In addition, the expression vectors used in this invention allow for the production of soluble Fab heterodimers as described in Example 5C.

A. Preparation of a Dicistronic Expression Vector, pComb3, Capable of Expressing a Phagemid Fab Display Protein The Pcomb3 phagemid expression vector of this invention is used in expressing the anti-hapten antibodies. The antibody Fd chain comprising variable ($V_H$) and constant ($C_H1$) domains of the heavy chain were fused with the C-terminal domain of bacteriophage gene III (3) coat protein. Gene III of filamentous phage encodes a 406-residue minor phage coat protein, cpiii (cp3), which is expressed prior to extrusion in the phage assembly process on a bacterial membrane and accumulates on the inner membrane facing into the periplasm of E. coli.

The phagemid vector, designated Pcomb3, allowed for both surface display and soluble forms of Fabs. The vector was originally designed for the cloning of combinatorial Fab libraries as described by Barbas et al., *Methods, A Companion to Methods in Enzymology*, 2:119–124 (1991), the disclosure of which is hereby incorporated by reference.

The Xho I and Spe I sites were provided for cloning complete PCR-amplified heavy chain (Fd) sequences. An Aat II restriction site is also present that allows for the insertion of Xho I/Aat II digests of the PCR products. The Sac I and Xba I sites were provided for cloning PCR amplified antibody light chains of this invention. The cloning sites were compatible with previously reported mouse and human PCR primers as described by Huse et al., *Science*, 246:1275–1281 (1989) and Persson et al., *Proc. Natl. Acad. Sci., USA*, 88:2432–2436 (1991). The nucleotide sequence of the pelB, a leader sequence for directing the expressed protein to the periplasmic space, was as reported by Huse et al., supra.

The vector also contained a ribosome binding site as described by Shine et al., *Nature*, 254:34 (1975). The sequence of the phagemid vector, pBluescript, which includes ColE1 and F1 origins and a beta-lactamase gene, has been previously described by Short et al., *Nuc. Acids Res.*, 16:7583–7600 (1988) and has the GenBank Accession Number 52330 for the complete sequence. Additional restriction sites, Sal I, Acc I, Hinc II, Cla I, Hind III, Eco RV, Pst I and Sma I, located between the Xho I and Spe I sites of the empty vector were derived from a 51 base pair stuffer fragment of Pbluescript as described by Short et al., supra. A nucleotide sequence that encodes a flexible 5 amino acid residue tether sequence which lacks an ordered secondary structure was juxtaposed between the Fab and cp3 nucleotide domains so that interaction in the expressed fusion protein was minimized.

Thus, the resultant combinatorial vector, Pcomb3, consisted of a DNA molecule having two cassettes to express one fusion protein, Fd/cp3, and one soluble protein, the light chain. The vector also contained nucleotide residue sequences for the following operatively linked elements listed in a 5' to 3' direction: a first cassette consisting of LacZ promoter/operator sequences; a Not I restriction site; a ribosome binding site; a pelB leader; a spacer region; a cloning region bordered by 5' Xho and 3' Spe I restriction sites; the tether sequence; the sequences encoding bacteriophage cp3 followed by a stop codon; a Nhe I restriction site located between the two cassettes; a second lacZ promoter/operator sequence followed by an expression control ribosome binding site; a pelB leader; a spacer region; a cloning region bordered by 5' Sac I and a 3' Xba I restriction sites followed by expression control stop sequences and a second Not I restriction site.

In the above expression vector, the Fd/cp3 fusion and light chain proteins were placed under the control of separate lac promoter/operator sequences and directed to the periplasmic space by pelB leader sequences for functional assembly on the membrane. Inclusion of the phage F1 intergenic region in the vector allowed for the packaging of single-stranded phagemid with the aid of helper phage. The use of helper phage superinfection allowed for the expression of two forms of cp3. Consequently, normal phage morphogenesis was perturbed by competition between the Fd/cp3 fusion and the native cp3 of the helper phage for incorporation into the virion. The resulting packaged phagemid carried native cp3, which is necessary for infection, and the encoded Fab fusion protein, which is displayed for selection. Fusion with the C-terminal domain was necessitated by the phagemid approach because fusion with the infective N-terminal domain would render the host cell resistant to infection.

The Pcomb3 expression vector described above forms the basic construct of the Fab display phagemid expression vectors described below used in this invention for the production of human anti-hapten Fab antibodies. The surface display phagemid expression vector, pC3AP313, was deposited with ATCC on Feb. 2, 1993 for use in this invention. The deposited vector has been assigned the ATCC Accession Number 75408. The pC3AP313 expression vector contained the bacteriophage gene III and heavy and light chain variable domain sequences for encoding human Fab antibodies against tetanus toxoid. The coding DNA strand nucleotide sequences of the anti-tetanus toxoid heavy and light chain variable domains in pC3AP313 are respectively listed in the Sequence Listing under SEQ ID NO 1 and 2. The reading frame of the nucleotide sequences for translation into amino acid residue sequences begins at nucleotide position 1 for both the light and heavy chain variable domains of pC3AP313. The tetanus toxoid-specific sequences were originally obtained from screening phage lambda vector combinatorial libraries of antibody heavy and light chains derived from the peripheral blood lymphocytes of an individual immunized with tetanus toxoid as described by Persson et al., supra, the disclosure of which is hereby incorporated by reference. Clone 3 was selected from the library screening and the heavy and light chain sequences were then respectively isolated by restriction digestion with Xho I/Spe I and Sac I/Xba I and ligated into a similarly digested Pcomb3 vector. The ligation procedure in creating expression vector libraries and the subsequent expression of the anti-hapten Fab antibodies is performed as described in Example 2.

2. Selection of Human Anti-Hapten Antibodies from Semisynthetic Light and Heavy Chain Libraries A. Preparation of Randomized Sites Within the Light Chain CDR3 of a Phagemid Fab Display Protein Produced by a Dicistronic Expression Vector 1) PCR with Coding Degenerate Oligonucleotide Primers Semisynthetic human Fab libraries in which both the CDR3 heavy and light chain domains were randomized were constructed, displayed on the surface of filamentous phage and selected for binding to three hapten conjugates. The phagemid expression vector, pC3AP313, containing heavy and light chain sequences for encoding a human antibody that immunoreacted with tetanus toxin, was used as a template for PCR.

Light chain libraries having CDR3 randomized in predetermined amino acid residue positions were prepared using the overlap PCR amplification protocols described herein. In the libraries, oligonucleotide primer pools were designed to result in the formation of CDR3 in lengths of 8, 9 and 10 amino acids to correspond to the naturally occurring loop lengths in humans. Diversity was limited to Kabat positions 92–96 as the remaining four positions are highly conserved in nature.

To amplify the 5' end of the light chain from framework 1 to the end of framework 3 of pC3AP313, the following primer pairs were used. The 5' coding (sense) oligonucleotide primer, KEF, having the nucleotide sequence 5'GAAT-TCTAAACTAGCTAGTCG3' (SEQ ID NO 3), hybridized to the noncoding strand of the light chain corresponding to the region 5' of and including the beginning of framework 1. The 3' noncoding (antisense) oligonucleotide primer, KV12B, having the nucleotide sequence 5'ATACTGCTGA-CAGTAATACAC3' (SEQ ID NO 4), hybridized to the coding strand of the light chain corresponding to the 3' end of the framework 3 region. The oligonucleotide primers were synthesized by Operon Technologies, Alameda, Calif. The terms coding or sense, used in the context of oligonucleotide primers, identifies a primer that is the same sequence as the DNA strand that encodes a heavy or light chain and that hybridizes to the noncoding strand. Similarly, the term noncoding or antisense identifies a primer that is complementary to the coding strand and thus hybridizes to it.

For overlap PCR, each set of PCR reactions were performed in a 100 microliter (ul) reaction containing 1 microgram (ug) of each of oligonucleotide primers listed above in a particular pairing, 8 ul 2.5 Mm dNTP's (DATP, DCTP, DGTP, DTTP), 1 ul Taq polymerase, 10 ng of template pC3AP313, and 10 ul of 10X PCR buffer purchased commercially (Promega Biotech, Madison, Wis.). Thirty-five rounds of PCR amplification in a Perkin-Elmer Cetus 9600 GeneAmp PCR System thermocycler were then performed. The amplification cycle consisted of denaturing at 94 degrees C (94C) for 1 minute, annealing at 47C for 1 minute, followed by extension at 72C for 2 minutes. To obtain sufficient quantities of amplification product, 15 identical PCR reactions were performed.

The resultant PCR amplification products were then gel purified on a 1.5% agarose gel using standard electroelution techniques as described in "Molecular Cloning: A Laboratory Manual", Sambrook et al., eds., Cold Spring Harbor, N.Y. (1989). Briefly, after gel electrophoresis, the region of the gel containing the DNA fragments of predetermined size was excised, electroeluted into a dialysis membrane, ethanol precipitated and resuspended in buffer containing 10 millimolar (Mm) Tris-Hcl [Tris(hydroxymethyl)aminomethane-hydrochloride] at Ph 7.5 and 1 Mm EDTA (ethylenediaminetetraacetic acid) to a final concentration of 50 nanograms/milliliter (ng/ml).

The purified amplification products were then used in an overlap extension PCR reaction with the products of the second PCR reaction, both as described below, to recombine the two products into reconstructed variable domain light chains containing the mutagenized third domain of the complementarity determining region (CDR3).

The second PCR reaction resulted in the amplification of the light chain from the 3' end of framework region 3 extending to the end of light chain constant region. To amplify this region for encoding a 4 random amino acid residue sequence in the CDR3 having a total length of 8 amino acids, the following primer pairs were used. The 5' coding oligonucleotide primer pool, designated KV4R, had the nucleotide sequence represented by the formula, 5'TAT-TACTGTCAGCAGTATNNKNNKNNKNN-KACTTTCGGCGGAGGGACCAAGG TGGAG3' (SEQ ID NO 5), where N can be A, C, G, or T and K is either G or T. The 3' noncoding primer, T7B, hybridized to the coding strand at the 3' end of the light chain constant domain having the sequence 5'AATACGACTCACTATAGGGCG3' (SEQ ID NO 6). The 5' end of the primer pool is complementary to the 3' end of framework 3 represented by the complementary nucleotide sequence of the oligonucleotide primer KV12B and the 3' end of the primer pool is complementary to the 5' end of framework 4. The region between the two specified ends of the primer pool is represented by a 12-mer NNK degeneracy. The second PCR reaction was performed on the pC3AP313 vector in a 100 ul reaction as described above containing 1 ug of each of oligonucleotide primers. The resultant PCR products encoded a diverse population of 4 mutagenized amino acid residues in a light chain CDR3 having a total of 8 amino acid residues. In the resultant CDR3, the 4 mutagenized amino acid residue positions were bordered on the amino terminal side by 3 amino acid residues that were left unchanged, Gln-Gln-Tyr, and on the carboxy terminal side by one amino acid residue, Thr. The products were then gel purified as described above.

An alternative oligonucleotide pool for preparing 4 randomized amino acid residues in a CDR3 having 8 amino acid residues was designated k8 having the formula 5'TAT-TACTGTCAGCAGTATNNKNNKNNKNN-KACTTTCGGCGGAGGGACC3' (SEQ ID NO 7). The k8 primer lacked 9 nucleotides from the 3' end of KV4R.

One hundred nanograms of gel purified products from the first and second PCR reactions were then admixed with 1 ug each of KEF and T7B oligonucleotide primers as a primer pair in a final PCR reaction to form a complete light chain fragment by overlap extension. The PCR reaction admixture also contained 10 ul of 10X PCR buffer, 1 ul Taq polymerase and 8 ul 2.5 Mm DNTP'S as described above.

To obtain sufficient quantities of amplification product, 15 identical overlap PCR amplifications were performed. The resulting light chain fragments beginning at framework 1 and extending to the end of constant region of the light chain thus contained a randomly mutagenized CDR3 region for encoding 4 new amino acid residues. The light chain fragment amplification products from the 15 reactions were first pooled and then gel purified as described above prior to their incorporation into the pC3AP313 surface display phagemid expression vector to form a library as described in Example 4A. The light chain library having a CDR3 of 8 amino acids resulting from amplifications with either KV4R or k8 was designated K8.

To create a randomized light chain CDR3 for encoding a CDR3 having a total of 9 amino acids in which 5 amino acid residues were randomized, the KV5R primer was used with the 3' primer, T7B, previously described. The KV5R had the formula 5'TATTACTGTCAGCAGTATNNKNNKNN-KNNKNNKACTTTCGGCGGAGGGACCA AGGTG-GAG3' (SEQ ID NO 8), where N is A, C, G or T and K is G or T.

An alternative oligonucleotide pool for preparing 5 randomized amino acid residues in a CDR3 having 9 amino acid residues was designated k9 having the formula 5'TAT-TACTGTCAGCAGTATNNKNNKNNKNN-KNNKACTTTCGGCGGAGGGACC3' (SEQ ID NO 9), where N is A, C, G or T and K is G or T. The k9 primer lacked 9 nucleotides from the 3' end of KV5R.

The resultant PCR products from amplifications with either KV5R or k9 encoded a diverse population of 5 mutagenized amino acid residues in a light chain CDR3 having a total of 9 amino acid residues. In the resultant CDR3, the 5 mutagenized amino acid residue positions were bordered on the amino terminal side by 3 amino acid residues that were left unchanged, Gln-Gln-Tyr, and on the carboxy terminal side by one amino acid residue, Thr. The light chain library having a CDR3 of 9 amino acids resulting from this amplification was designated K9.

To create a randomized light chain CDR3 for encoding a CDR3 having a total of 10 amino acids in which 6 amino acid residues were randomized, the KV6R primer was used with the 3' primer, T7B, previously described. The KV6R primer had the formula 5'GATTTTGCAGTGTATTACTGT-CAGCAGTATNNKNNKNNKNNKNNKACTT TCGGCGGAGGGACCAAGGTGGAG3' (SEQ ID NO 10), where N is A, C, G or T and K is G or T.

An alternative oligonucleotide pool for preparing 6 randomized amino acid residues in a CDR3 having 10 amino acid residues was designated k10 having the formula 5'TAT-TACTGTCAGCAGTATNNKNNKNN-KNNKNNKACTTTCGGCGGAGGGA CC3', where N is A, C, G or T and K is G or T (SEQ ID NO 11). The k10 primer was shortened on both the 5' and 3' ends of the KV6R primer by 12 and 9 nucleotides, respectively.

The resultant PCR products from amplifications with either KV6R or k10 encoded a diverse population of 6 mutagenized amino acid residues in a light chain CDR3 having a total of 10 amino acid residues. The light chain library having a CDR3 of 10 amino acids resulting from this amplification was designated K10. In the resultant CDR3, the 6 mutagenized amino acid residue positions were bordered on the amino terminal side by 3 amino acid residues that were left unchanged, Gln-Gln-Tyr, and on the carboxy terminal side by one amino acid residue, Thr.

To create a randomized light chain CDR3 for encoding a CDR3 having a total of 10 amino acids in which all 10 amino acid residues were randomized, the KV10R primer was used with the 3' primer, T7B, previously described. The KV10R primer had the formula 5'GATTTTGCAGTGTATTACTGT-NNKNNKNNKNNKNNKNNKNNKNNKNNKT TCGGCGGAGGGACCAAGGTGGAG3' (SEQ ID NO 12), where N is A, C, G or T and K is G or T.

The resultant PCR products encoded a diverse population of 10 mutagenized amino acid residues in a light chain CDR3 having a total of 10 amino acid residues. The light chain library having a CDR3 of 10 amino acids resulting from this amplification was designated K10'.

2) PCR with Noncoding Degenerate Oligonucleotide Primers

Additional semisynthetic human Fab libraries in which both the heavy and light chain CDR3 were randomized were constructed, displayed on the surface of filamentous phage and selected for binding to three hapten conjugates. Another way of introducing randomized nucleotides into a template DNA sequence for encoding amino acid residue substitutions or additions was to use noncoding degenerate primers instead of using coding degenerate oligonucleotide primers as described above in Example 2A1). The coding (sense)

degeneracy had the formula 5'-NNK-3', where N can be either A, C, G or T and K is either G or T. For use in this invention, the noncoding (antisense) oligonucleotide primers used in overlap PCR procedures had the degeneracy formula 5'-MNN-3' written in the conventional 5' to 3' direction, where M is equal to either A or C. Written in 3' to 5' direction, the noncoding oligonucleotide had the formula 3'-NNM-5' which is that complementary sequence to the coding formula 5'-NNK-3'. Thus, the noncoding oligonucleotide primers used in this invention provided for incorporating the same coding sequence degeneracies as the coding oligonucleotide primers. In other words, the same semisynthetic library having a particular CDR randomized arrangement can be obtained by using overlap PCR with predetermined coding or noncoding primers. The use of a noncoding primer also requires the use of different overlap primers as described herein.

The resultant PCR products were also prepared from the phagemid expression vector, pC3AP313, containing heavy and light chain sequences for encoding a human antibody that immunoreacted with tetanus toxin.

Light chain libraries having CDR3 randomized in predetermined amino acid residue positions were prepared using the overlap PCR amplification protocols described herein. In the libraries, oligonucleotide primer pools were designed to result in the formation of CDR3 in lengths of 8, 10 and 16 amino acids in length. For all three libraries, the CDR3 was completely randomized using the noncoding degeneracy 5'-MNN-3' that was complementary to the coding degeneracy 5'-NNK-3' as used in primers described in Example 2A1).

To amplify the 5' end of the light chain from framework 1 to the end of CDR3 of pC3AP313 and to incorporate degenerate nucleotide sequences into the amplified DNA, the following primer pairs were used. The 5' coding (sense) oligonucleotide primer, KEF, having the nucleotide sequence 5'GAATTCTAAACTAGCTAGTCG3' (SEQ ID NO 3), hybridized to the noncoding strand of the light chain corresponding to the region 5' of and including the beginning of framework 1. Three separate noncoding (antisense) oligonucleotide primer pools were designed to prepare light chain CDR3 libraries having 8, 10 or 16 randomized amino acid residues. The degenerate oligonucleotides overlapped with the 3' end of framework region 3 through the CDR3 into the 5' end of framework region 4.

The primer pool designated p313K38OVb for incorporating 8 randomized amino acid residues had the noncoding nucleotide sequence written in the 5' to 3' direction, 5'GTTCCACCTTGGTCCCTTGGCCGAAMN-NMNNMNNMNNMNNMNNMNNMNNACA GTAGTACACTGCAAAATC3', where M is either A or C, and N can be A, C, G or T (SEQ ID NO 13). The light chain library formed from this amplification was designated CDR3-LCNC8. The primer pool, designated p313K3100Vb, for incorporating 10 randomized amino acid residues had the noncoding nucleotide sequence written in the 5' to 3' direction, 5'GTTCCACCTTGGTCCCTTGGC-CGAAMNNMNNMNNMNNMNNMNNMNNMNNMNN MNNACAGTAGTACACTGCAAAATC3', where M is either A or C, and N can be A, C, G or T (SEQ ID NO 14). The light chain library formed from this amplification was designated CDR3-LCNC10. The primer pool designated p313K3160Vb for incorporating 16 randomized amino acid residues had the noncoding nucleotide sequence written in the 5' to 3' direction, 5'GTTCCACCTTGGTCCCTTGGC-CGAAMNNMNNMNNMNNMNNMNNMNNMNNMNN MNNMNNMNNMNNMNNMNNMNNACAGTAGTACA-CTGCAAAATC3', where M is either A or C, and N can be A, C, G or T (SEQ ID NO 15). The light chain library formed from this amplification was designated CDR3-LCNC16.

Three separate first PCR amplifications were then performed with the KEF primer paired with each of the three noncoding degenerate primers listed above. The amplifications were performed as described in Example 2A1).

The second PCR amplification resulted in the amplification of the light chain from the 5' end of framework region 4 extending to the end of light chain constant region. The 5' coding oligonucleotide, designated p313KF40F, had the nucleotide sequence 5'TTCGGCCAAGGGACCAAGGTG-GAAC3' (SEQ ID NO 16). This primer began at the 5' end of framework region 4 providing an overlapping region with the corresponding region in the degenerate oligonucleotide primers. The 3' noncoding primer, T7B, hybridized to the coding strand at the 3' end of the light chain constant domain having the sequence 5'AATACGACTCACTATAGGGCG3' (SEQ ID NO 6). The second PCR reaction was performed as described above.

For overlap PCR, 100 ng of the amplification products from the first and second reactions were pooled following purification and a third round of PCR was performed using the primer pair, KEF and T7B, as described above to form a complete light chain fragment by overlap extension. The light chain fragment amplification products from 15 parallel reactions were first pooled and then gel purified as described above prior to their incorporation into the pC3AP313 surface display phagemid expression vector to form a library as described in Example 4A. The resultant semisynthetic light chain libraries encoded a CDR3 of 8, 10 or 16 randomized amino acids.

The formulations for the various light chain oligonucleotide primers based on the individual oligonucleotide primers presented herein are shown in the Claims and have the corresponding SEQ ID Nos from 26 to 31.

B. Preparation of Randomized Sites Within the Heavy Chain CDR3 of a Phagemid Fab Display Protein Produced by a Dicistronic Expression Vector Heavy chain libraries having randomized CDR3 in lengths of 5, 10 and 16 amino acids were also prepared using the pC3AP313 surface display expression vector as the PCR template. The resultant libraries prepared as described below were then crossed with the K8, K9 and K10 light chain libraries prepared in Example 2A1). The heavy chain CDR3 (HCDR3) having 10 amino acid residues is approximately the average length utilized in human antibodies. CDR3 having 5 and 16 amino acid residues were chosen to be representative of short and long CDRs respectively based on a previous report on the genetic diversity in this region. Complete randomization using an NNK or NNS degeneracy yielded libraries designated 5, 10 and 16.

Alternatively, the penultimate position of the HCDR3 was fixed as aspattic acid yielding libraries designated G, F and E, respectively. 5, 10 and 16 amino acid residue CDR3s. The first position of the F and E libraries was also fixed as a glycine residue encoded by the triplet codon GGT. The penultimate aspartic acid, Kabat position 101, is conserved in 75% of human antibodies as described by Kabat et al., supra, the disclosure of which is hereby incorporated by reference. The Kabat 101 position is thought to be structurally significant in stabilizing the immunoglobulin loop structure as described by Chothia et al., *J. Mol. Biol.,*

196:901–917 (1987), the disclosure of which is hereby incorporated by reference.

The following amplifications were performed for preparing heavy chain G, F and E libraries. The first PCR reaction resulted in the amplification of the region of the heavy chain fragment in the pC3AP313 phagemid beginning at framework region 1 and extending to the end of framework region 3 which was located 5' to CDR3. The degenerate primer pools designed for use with the pC3AP313 template resulted in the retention of a conserved aspartic acid residue in the next to last position in the CDR3 for all 3 lengths of CDR3s prepared. The retention of the aspartic acid residue in this position is preferred for use in this invention as the expressed proteins containing this residue exhibit high affinity binding characteristics.

To amplify the 5' end of the heavy chain from framework 1 to the end of framework 3, the following primer pairs were used. The 5' coding oligonucleotide primer, FTX3, having the nucleotide sequence 5'GCAATTAACCCTCAC- TAAAGGG3' (SEQ ID NO 17), hybridized to the noncoding strand of the heavy chain corresponding to the region 5' of and including the beginning of framework 1. The 3' non- coding oligonucleotide primer, BFR3U, having the nucle- otide sequence 5'TCTCGCACAGTAATACACGGCCGT3' (SEQ ID NO 18), hybridized to the coding strand of the heavy chain corresponding to the 3' end of the framework 3 region. The oligonucleotide primers were synthesized by Operon Technologies.

The PCR reaction was performed as described in Example 2A1). The resultant PCR amplification products were then gel purified as described and used in an overlap extension PCR reaction with the products of the second PCR reaction, both as described below, to recombine the two products into reconstructed heavy chains containing mutagenized CDR3s.

The second PCR reaction resulted in the amplification of the heavy chain from the 3' end of framework region 3 extending to the end of $C_H1$ region. To amplify this region for encoding a 5 random amino acid residue sequence having an aspattic acid in the fourth position in the CDR3, the following primer pairs were used. The 5' coding oligo- nucleotide primer pool, designated HCDRD5, had the nucle- otide sequence represented by the formula, 5'GCCGTGTATTACTGTGCGAGANNKNNKNNKGAC- NNKTGGGGCCAAGGGACCACGGTC3' (SEQ ID NO 19), where N can be A, C, G, or T and K is either G or T. The 5' end of the primer pool is complementary to the 3' end of framework 3 represented by the complementary nucle- otide sequence of the oligonucleotide primer BFR3U and the 3' end of the primer pool is complementary to the 5' end of framework 4. The region between the two specified ends of the primer pool is represented by a 12-mer degeneracy of 4 NNK triplets plus a sequence encoding a conserved aspattic acid residue one position from the end of the CDR3. The 3' noncoding oligonucleotide primer, R3B, having the nucle- otide sequence 5'TTGATATTCACAAACGAATGG3' (SEQ ID NO 20), hybridized to the coding strand of the heavy chain corresponding to the 3' end of $C_H1$.

The sequence 5'-NNK-3' represents the coding strand sequence having the complementary sequence 3'-NNM-5' in the primer as read from the 3' to 5' direction. Thus, in the primer as listed below the noncoding strand sequence is 5'-MNN-3' as read in the 5' to 3' direction. The coding triplet sequence 5'-NNK-3' was designed to prevent the production of deleterious stop condos. The only stop codon that could result from the expression of NNK would be an amber mutation that is suppressed when the phagemid is expressed an amber-suppressing host cell, preferably *E. coli* supE strain.

The second PCR reaction was then performed on the pC3AP313 in an 100 ul reaction as described above con- taining 1 ug of each of oligonucleotide primers HCDRD5 and R3B. The resultant PCR products encoded a diverse population of mutagenized CDR3s of 5 amino acid residues in length with a conserved aspattic acid residue in the fourth amino acid residue position in the CDR3. The products were then gel purified as described above.

One hundred nanograms of gel purified products from the first and second PCR reactions were then admixed with 1 ug each of FTX3 and R3B oligonucleotide primers as a primer pair in a final PCR reaction to form a complete heavy chain fragment by overlap extension. The PCR reaction admixture also contained 10 ul 10X PCR buffer, 1 ul Taq polymerase and 8 ul 2.5 Mm DNTP'S as described above. The PCR reaction was performed as previously described.

To obtain sufficient quantities of amplification product, 15 identical PCR reactions were performed. The resulting heavy chain fragments began at framework 1 and extended to the end of $C_H1$ and had a randomly mutagenized CDR3 for encoding 5 amino acid residues with a conserved aspartic acid residue. The heavy chain fragment amplification prod- ucts from the 15 reactions were first pooled and then gel purified as described above prior to their incorporation into a digested pC3AP313 surface display phagemid expression vector to form a library as described in Example 4B. The resulting CDR3-randomized heavy chain phagemid library was designated library G.

In addition to randomizing the CDR3 in pC3AP313 for expressing 5 amino acid residues, PCR amplifications were performed for expressing a CDR3 containing 10 amino acid residues. Two separate PCR amplifications were performed as described above with the only exception being that, in the second reaction, the 5' coding degenerate primer, designated HCDRD10, used to encode 10 amino acid residues com- prising the heavy chain CDR3. The degenerate 5' coding primer used here was designed to retain the first amino acid position of a glycine residue in the pC3AP313 template and incorporate a conserved aspattic acid residue in the ninth amino acid position. The HCDRD10 primer had the for- mula: 5'GCCGTGTATTACTGTGCGAGAGGTNN- KNNKNNKNNKNNKNNKNNKGACNNKT GGGGC- CAAGGGACCACGGTC3' (SEQ ID NO 21), where N is A, C, G or T and K is G or T. The amino acid sequences comprising the CDR3 encoded by the use of the HCDRD10 primer had an aspattic acid residue conserved in the ninth position of the CDR3. The resultant products were pooled and purified as described above prior to insertion into a digested pC3AP313 surface display phagemid expression vector to form a library as described in Example 4B. The resulting CDR3-randomized heavy chain phagemid library was designated library F.

PCR amplifications using the template pC3AP313 were also performed for expressing a randomized CDR3 contain- ing 16 amino acid residues. The degenerate 5' coding primer used for this amplification was designed to retain the first amino acid position of a glycine residue in the pC3AP313 template and incorporate a conserved aspattic acid residue in the fifteenth amino acid position. Two separate PCR ampli- fications were performed as described above for the CDR3 having 5 amino acids with the only exception being that, in the second reaction, the 5' coding degenerate primer, des- ignated HCDRD16, used to encode 16 random amino acid residues had the formula: 5'GCCGTGTATTACTGTGC- GAGAGGTNNKNNKNNKNNKNNKNNN- KNNKNNKN NKNNKNNKNNKGACNNKTGGGGC- CAAGGGACCACGGTC3' (SEQ ID NO 22), where N is A, C, G or T and K is G or T. The amino acid sequences comprising the CDR3 encoded by the use of the HCDRD16 primer had an aspartic acid conserved in position 15. The resultant products were pooled and purified as described above prior to insertion into a digested pC3AP313 surface display phagemid expression vector to form a library as described in Example 4B. The resulting phagemid library was designated library E.

As described above, the resultant randomized heavy chain CDR3s of various lengths having a conserved aspartic acid residue in the penultimate position amplified from pC3AP313 were purified, digested and ligated back into pC3AP313 for preparation of separate expression libraries as described in Example 4B.

In similar overlap PCR amplifications, heavy chain libraries having completely randomized CDR3s in lengths of 5, 10 or 16 were prepared. The degenerate oligonucleotide pool for preparing the CDR3-HC5 library had the nucleotide formula 5'GTGTATTATTGTGCGAGANNSNNSNNSNNSNNST-GGGGCCAAGGGACCACG3', where N can be either A, C, G or T and S is either G or C (SEQ ID NO 23). The resultant library was designated CDR3-HC5. The degenerate oligonucleotide pool for preparing the CDR3-HC10 library had the nucleotide formula 5'GTGTATTATTGTGCGAGANNS-NNSNNSNNSNNSNNSNNSNNSNNSNNSTGGGGCCA-AGGGACCACG3', where N can be either A, C, G or T and S is either G or C (SEQ ID NO 24). The resultant library was designated CDR3-HC10. The degenerate oligonucleotide pool for preparing the CDR3-HC16 library, designated 7ECDR3, had the nucleotide formula 5'GTGTATTATTGT-GCGAGANNSNNSNNSNNSNNSNNSNNSNNSNNSNN-SNNSN NSNNSNNSNNSNNSTGGGGCCAAGGGACC-ACG3', where N can be either A, C, G or T and S is either G or C (SEQ ID NO 25). The resultant library was designated CDR3-HC16. As described above, the resultant completely randomized heavy chain CDR3s of various lengths amplified from pC3AP313 were then purified, digested and ligated back into a digested pC3AP313 expression vector for preparation of an expression library as described in Example 4B.

3. Preparation of Heavy and Light Chain Expression Vector Libraries Having a Universal Light Chain

A. Crossed Random Heavy Chain Libraries with a Universal Light Chain

In order to obtain expressed human Fab antibody libraries comprised of a population of random heavy chain fragments and a single universal light chain, crossed phagemid libraries are constructed. The libraries provide for the expression of recombinant human Fab antibodies having a population of random heavy chains and a single universal light chain for selection of Fab antibodies that bind preselected ligands with high affinity. Libraries in which heavy chains are random are prepared as described in Barbas, et al., *Proc. Natl. Acad. Sci. USA*, 88:7978–7982 (1991). The pC3AP313 vector containing a universal light chain is digested with Xho I and Spe I to remove the pC3AP313 natural heavy chain and replace it with Xho I and Spe I digests of the random heavy chain library. Alternatively, libraries in which heavy chains are random are prepared by digestion of the p6F vector described in Example 8 containing a different universal light chain with Xho I and Spe I to remove the p6F natural heavy chain and replace it with Xho I and Spe I digests of a random heavy chain library. To verify the presence of random heavy chains and a universal light chain, randomly selected clones from each crossed library are sequenced.

B. Crossed Randomized CDR Heavy Chain Libraries with Universal Light Chain

Alternatively, expressed human Fab antibody libraries comprised of a population of randomized CDR heavy chain fragments and a single universal light chain, can also be obtained by the construction of crossed phagemid libraries. The libraries provide for the expression of recombinant human Fab antibodies having randomized CDR heavy chains and a single universal light chain for the selection of Fab antibodies that bind preselected ligands with high affinity.

Libraries in which the CDR3 region of the heavy chain is randomized are prepared as described in Example 4B. Alternatively, the CDR1 or CDR2 region of the heavy chain is randomized by the methods taught in Example 4B. In addition, a library of heavy chains having one or more randomized CDR region created to generate even greater diversity of the heavy chain CDR regions is contemplated. The pC3AP313 vector containing the universal light chain is digested with Xho I and Spe I to remove the pC3AP313 natural heavy chain and the Xho I and Spe I digests of the randomized heavy chain libraries are combined randomly (crossed) into the digested pC3AP31V vector to form a population of vectors having the universal light chain and one of the randomized heavy chains from the heavy chain library. Crossed libraries are thus prepared by the combination of a universal light chain with a randomized heavy chain library. To verify the presence of randomized heavy chains and a single universal light chain, randomly selected clones from each crossed library are sequenced.

4. Preparation of Heavy and Light Chain Expression Vector Libraries Having Randomized CDR3

A. Light Chain Libraries

The light chains having randomized CDR3 from the overlap PCR amplifications using both coding and noncoding degenerate oligonucleotide primers produced in Example 2A were then separately introduced into the pC3AP313 Pcomb3-based monovalent Fab phage display vector prepared as described in Example 1. The PCR products resulting from each of the amplifications prepared in Example 2A were separately inserted into a phagemid expression vector to prepare phagemid libraries. As described below, the resultant gel purified light chain PCR CDR3-randomized products prepared in Example 2A were digested with restriction enzymes and separately ligated into the pC3AP313 phagemid expression vector that was similarly digested.

For preparation of phagemid libraries for expressing the light chain PCR products prepared in Example 2A, the PCR products were separately digested with Sac I and Aat II and separately ligated with a similarly digested pC3AP313 phagemid expression vector prepared as described in Example 1. Digestion of the pC3AP313 vector with Sac I and Aat II removed the nucleotide sequence region beginning at the 5' end of the native light chain variable domain to the beginning of framework 4. The ligation thus resulted in operatively linking the light chain framework 1 through randomized CDR3 PCR products with the native framework 4 domain present in the pC3AP313 vector. The expression of the resultant light chain libraries was under the control of a LacZ promoter and pelB leader sequence.

Phagemid libraries for expressing each of the Fabs having randomized light chain CDR3 of this invention were prepared in the following procedure. To form circularized vectors containing the PCR product insert, 640 ng of the digested PCR products was admixed with 2 ug of the linearized pC3AP313 phagemid vector and ligation was allowed to proceed overnight at room temperature using 10 units of BRL ligase (Gaithersburg, Md.) in BRL ligase buffer in a reaction volume of 150 ul. Five separate ligation reactions were performed to increase the size of the phage library having randomized CDR3. Following the ligation reactions, the circularized DNA was precipitated at $-20C$ for 2 hours by the admixture of 2 ul of 20 mg/ml glycogen, 15 ul of 3M sodium acetate at Ph 5.2 and 300 ul of ethanol. DNA was then pelleted by microcentrifugation at 4C for 15 minutes. The DNA pellet was washed with cold 70% ethanol and dried under vacuum. The pellet was resuspended in 10 ul of water and transformed by electroporation into 300 ul of *E. coli* XL1-Blue cells to form a phage library. The total yield from the PCR amplification and transformation procedure described herein was approximately $10^8$ independent transformants.

The light chain libraries having randomized CDR3 of 4, 5, 6 and 10 amino acid residues (respectively in a CDR3 of 8, 9, 10 and 10 amino acid residues) resulting from the PCR products obtained with the coding degenerate primer pool were respectively designated K8, K9, K10 and K10'. The light chain libraries having CDR3 of 8, 10 and 16 amino acid residues resulting from the PCR products obtained with the noncoding degenerate primer pool were respectively designated CDR3-LCNC8, CDR3-LCNC10 and CDR3-LCNC16.

B. Heavy Chain Libraries

The heavy chains having randomized CDR3 produced in Example 2B from overlap PCR amplifications were then separately introduced into the monovalent Fab phage display vector Pcomb3 prepared as described in Example 1. The PCR products resulting from each of the amplifications prepared in Example 2B were separately inserted into a phagemid expression vector to prepare phagemid libraries. As described below, the resultant gel purified light chain PCR fragments prepared in Example 2B were digested with the restriction enzymes and separately ligated into the pC3AP313 phagemid expression vector that was similarly digested.

For preparation of phagemid libraries for expressing the heavy chain PCR products prepared in Example 2B, the PCR products were digested with Xho I and Spe I and separately ligated with a similarly digested pC3AP313 phagemid expression vector prepared as described in Example 1. Digestion of the pC3AP313 vector with Xho I and Spe I removed the native nucleotide sequence region beginning at the 5' end of the heavy chain variable domain to the beginning of the heavy chain constant domain, $C_H1$. The ligation thus resulted in operatively linking the framework 1 through randomized CDR3 PCR products with the native $C_H1$ domain present in the pC3AP313 vector. The expression of the resultant heavy chain libraries was under the control of a LacZ promoter and pelB leader sequence.

Phagemid libraries for expressing each of the Fabs having randomized heavy chain CDR3 of this invention were prepared as described above for the light chain. The total yield from the PCR amplification and transformation procedure described herein was approximately $10^8$ independent transformants.

The heavy chain libraries with CDR3 of 5, 10 or 16 amino acid residues in length resulting from the PCR products obtained retaining an aspattic acid in the penultimate position were respectively designated G, F and E. The heavy chain libraries with completely randomized CDR3 of 5, 10 or 16 amino acid residues in length were respectively designated CDR3-HC5, CDR3-HC10 and CDR3-HC16.

C. Crossed Heavy and Light Chain Libraries

In order to obtain expressed human Fab antibodies having both randomized heavy and light chain fragments, crossed phagemid libraries were constructed. The libraries provided for the expression of recombinant human Fab antibodies having heavy and light chains in which the CDR3 in both were selectively randomized for selection of Fab antibodies that bind synthetic haptens with high affinity. Libraries in which both CDR3s were randomized were prepared by digestion of the light chain libraries prepared in Example 4A with Xho I and Spe I to remove the pC3AP313 natural heavy chain and replace it with Xho I and Spe I digests of the synthetic heavy chain libraries prepared in Example 4B. Nine crossed libraries were prepared by combination of KS, K9 and K10 light chain libraries with the G, F and E heavy chain libraries. In addition, to examine the role of the light chain CDR3, the heavy chain domain of a previously selected clone that encoded a Fab antibody, designated F22, that reacted with fluorescein was crossed with the light chain KS, K9 and K10 libraries. Crossed libraries were designated by listing the light chain library first separated from the heavy chain library by a slash, e.g., K8/F. All resultant crossed libraries consisted of at least $10^8$ independent transformants except for K9/F22 and K8/F22 that contain $10^7$ transformants. The crossed library designated K10/E consisted of Fab fragments were 20 positions were randomized. In order for the crossed libraries to be "complete", i.e., where all possible members (combinations of heavy and light chain library members) are represented, more than $10^{30}$ transformants would be necessary. To verify the targeted mutagenesis of the light and heavy chain CDR3, randomly selected clones from each uncrossed library were sequenced prior to crossing.

The other light chain libraries, K10', CDR3-LCNC8, CDR3-LCNC10 and CDR3-LCND16 are similarly crossed with all of the heavy chain libraries prepared in Example 4B to form additional crossed libraries having varying lengths of CDR3 having varying randomized amino acid residues.

D. Crossed CDR3 Randomized Heavy Chain and A Single Universal Light Chain Libraries In order to obtain expressed human Fab antibodies having randomized heavy and universal light chain fragments, crossed phagemid libraries are constructed. The libraries provide for the expression of recombinant human Fab antibodies having heavy chains in which the CDR3 are randomized for the selection of Fab antibodies that bind preselected ligands with high affinity. The libraries also provide for the expression of recombinant human Fab antibodies having a single universal light chain for the selection of Fab antibodies that bind preselected ligands with high affinity. Libraries in which CDR3 of the heavy chain are randomized, are prepared by digestion of the universal light chain with Xho I and Spe I to remove the pC3AP313 natural heavy chain and replace it with Xho I and Spe I digests of the synthetic heavy chain libraries prepared in Example 4B. Crossed libraries are prepared by combination of a universal light chain, with the amino acid sequence as shown in SEQ NO 2, with the G, F and E heavy chain libraries. The crossed library consists of Fab fragments where 5, 10, or 16 positions of the heavy chain CDR3 are randomized and a single universal light chain. To verify the targeted mutagenesis of the heavy chain CDR3, randomly selected clones from each uncrossed library are sequenced prior to crossing.

Another universal light chain, 6F with the nucleotide sequence as shown in SEQ ID NO 62, is similarly crossed with all of the heavy chain libraries prepared in Example 4B to form additional crossed libraries having varying lengths of heavy chain CDR3 with varying randomized amino acid residues and a single universal light chain.

5. Selection of Anti-Hapten Fab Antibodies Expressed on Phage

A. Preparation of Phage Expressing Semisynthetic Fab Heterodimers

After transformation, to isolate phage expressing Fabs reactive with synthetic haptens, panning on target synthetic haptens was performed as described in Example 5B below.

Phage were first prepared on which the semisynthetic Fab antibodies were expressed for selecting on synthetic haptens. Three ml of SOC medium (SOC was prepared by admixture of 20 grams (g) bacto-tryptone, 5 g yeast extract and 0.5 g NaCl in 1 liter of water, adjusting the Ph to 7.5 and admixing 20 ml of glucose just before use to induce the expression of the heavy chain domain anchored to the phage coat protein 3 (Fd-cpiii) and soluble light chain heterodimer) were admixed to selected phage libraries and the culture was shaken at 220 rpm for 1 hour at 37C. Then 10 ml of SB (SB was prepared by admixing 30 g tryptone, 20 g yeast extract, and 10 g Mops buffer per liter with Ph adjusted to 7) containing 20 ug/ml carbenicillin and 10 ug/ml tetracycline were admixed and the admixture was shaken at 300 rpm for an additional hour. This resultant admixture was admixed to 100 ml SB containing 50 ug/ml carbenicillin and 10 ug/ml tetracycline and shaken for 1 hour, after which helper phage VCSM13 ($10^{12}$ pfu) were admixed and the admixture was shaken for an additional 2 hours. After this time, 70 ug/ml kanamycin was admixed and maintained at 30C overnight. The lower temperature resulted in better heterodimer incorporation on the surface of the phage. The supernatant was cleared by centrifugation (4000 rpm for 15 minutes in a JA10 rotor at 4C). Phage were precipitated by admixture of 4% (w/v) polyethylene glycol 8000 and 3% (w/v) NaCl and maintained on ice for 30 minutes, followed by centrifugation (9000 rpm for 20 minutes in a JA10 rotor at 4C). Phage pellets were resuspended in 2 ml of PBS and microcentrifuged for three minutes to pellet debris, transferred to fresh tubes and stored at −20C for subsequent screening as described below.

For determining the titering colony forming units (cfu), phage (packaged phagemid) were diluted in SB and 1 ul was used to infect 50 ul of fresh ($A_{OD600}$=1) E. coli XL1-Blue cells grown in SB containing 10 ug/ml tetracycline. Phage and cells were maintained at room temperature for 15 minutes and then directly plated on LB/carbenicillin plates.

B. Selection of the Phagemid-Displayed Semisynthetic Fab Heterodimers

1) Multiple Pannings of the Phage Library Having Phagemid Fab-Displayed Synthetic Binding Site Proteins The phage libraries produced in Example 4A, 4B and 4C were panned as described herein on microtiter plates coated with the synthetic hapten conjugate target molecules. Three synthetic haptens were chosen for screening for improved high affinity antibodies having either a randomized heavy or light chain domain or both. The conjugates, shown in FIG. 1 and labeled as 1, 2, and 3, respectively, were fluorescein-BSA (F1-BSA), S-BSA, an analog for the selection of catalytic antibodies that catalyze a decarboxylation reaction, and C-BSA, similar to the other two haptens but containing a flat aromatic ring system and lacking the anionic character of the other haptens. Conjugate 1 was described by Barbas et al., *Proc. Natl. Acad. Sci., USA*, 89:4457–4461 (1992), the disclosure of which is hereby incorporated by reference. Conjugates 2 and 3 have been previously described by Lewis et al., *Reports*, 1019–1021 (1991), the disclosure of which is hereby incorporatedby reference. The reagents were used at a concentration of 40 ug/ml in the coating buffer, 0.1M bicarbonate at Ph 8.6.

The panning procedure described was a modification of that originally described by Parmley et al., *Gene*, 73:305–318 (1988). This procedure, described below for one preparation, was followed for each of the phage preparations for all libraries prepared for use in this invention. Since the haptens were conjugated to BSA, selective pressure was applied to select for hapten binding and against BSA binding. This was accomplished by resuspending phage in TBS containing 1% BSA prior to selection and by alternating 3% BSA and 2% non-fat dry milk blocking of the microtiter dish at each round of selection.

Wells of a microtiter plate (Costar 3690) were separately coated overnight at 4C with the purified target conjugates prepared above. The wells were washed twice with water and blocked by completely filling the well with 3% (w/v) bovine serum albumin (BSA) in PBS and incubating the plate at 37C for 1 hour. Blocking solution was removed by shaking. 50 ul of each of the phage libraries prepared above (typically $10^{11}$ cfu) were added to each well, and the plate was incubated for 2 hours at 37C.

Phage were removed and the plate was washed once with water. Each well was then washed 10 times with TBS/Tween (50 mM Tris-HCl at pH 7.5, 150 mMNaCl, 0.5% Tween 20) over a period of 1 hour at room temperature then pipetted up and down to wash the well, each time allowing the well to remain completely filled with TBS/Tween between washings. The plate was washed once more with distilled water and adherent phage were eluted by the addition of 50 ul of elution buffer (0.1M Hcl, adjusted to Ph 2.2 with solid glycine, containing 1 mg/ml BSA) to each well and incubation at room temperature for 10 minutes. The elution buffer was pipetted up and down several times, removed, and neutralized with 3 ul of 2M Tris base per 50 ul of elution buffer used.

Eluted phage were used to infect 2 ml of fresh ($OD_{600}$=1) E. coli XL1-Blue cells for 15 minutes at room temperature, after which 10 ml of SB containing 20 ug/ml carbenicillin and 10 ug/ml tetracycline was admixed. Aliquots of (20, 10, and 1/10 ul were removed for plating to determine the number of phage (packaged phagemids) that were eluted from the plate. The culture was shaken for 1 hour at 37C, after which it was added to 100 ml of SB containing 50 ug/ml carbenicillin and 10 ug/ml tetracycline and shaken for 1 hour. Eelper phage VCSM13 ($10^{12}$ pfu) were then added and the culture was shaken for an additional 2 hours. After this time, 70 ug/ml kanamycin was added and the culture was incubated at 37C overnight. Phage preparation and further panning were repeated as described above.

Following each round of panning, the percentage yield of phage were determined, where % yield—(number of phage eluted/number of phage applied) X 100.

The final phage output ratio was determined by infecting 2 ml of logarithmic phase XL1-Blue cells as described above and plating aliquots on selective plates. Following the washing and acid elution from the first round of panning, the phage-displayed Fab libraries were then combined in subsequent rounds of panning to identify by competitive binding the highest affinity clones from the collection of libraries. By sequencing the selected binders, the source library of the clones was then determined.

From this procedure, clones were selected from each of the Fab libraries for their ability to bind to their respective selected synthetic targets. The panned phage surface libraries were then converted into ones expressing soluble semisynthetic Fab antibodies for further characterization as described in Example 5C.

C. Preparation of Soluble Fab-Displayed Binding Site Proteins

In order to further characterize the specificity of the semisynthetic Fab antibodies expressed on the surface of phage as described above, soluble heterodimers were prepared and analyzed in ELISA assays on synthetic conjugate target-coated plates and by competitive ELISA with increasing concentrations of soluble competitor protein as described below.

To prepare soluble Fabs consisting of heavy and light chains (i.e., heterodimers), phagemid DNA from positive clones selected in Example 5B above was isolated and digested with Spe I and Nhe I. Digestion with these enzymes produced compatible cohesive ends. The 4.7 kb DNA fragment lacking the gIII portion was gel-purified (0.6% agarose) and self-ligated. Transformation of $E.$ $coli$ XL1-Blue afforded the isolation of recombinants lacking the gIII fragment. Clones were examined for removal of the gIII fragment by Xho I/Xba I digestion, which should yield an 1.6 kb fragment. Clones were grown in 100 ml SB containing 50 ug/ml carbenicillin and 20 Mm $MgCl_2$ at 37C until an $OD_{600}$ of 0.2 was achieved. IPTG (1 Mm) was added and the culture grown overnight at 30C (growth at 37C provides only a light reduction in heterodimer yield). Cells were pelleted by centrifugation at 4000 rpm for 15 minutes in a JA10 rotor at 4C. Cells were resuspended in 4 ml PBS containing 34 ug/ml phenylmethylsulfonyl fluoride (PMSF) and lysed by sonication on ice (2–4 minutes at 50% duty). Debris was pelleted by centrifugation at 14,000 rpm in a JA20 rotor at 4C for 15 minutes. The supernatant was used directly for ELISA analysis and was stored at –20C. For the study of a large number of clones, 10-ml cultures provided a sufficient amount of the semisynthetic Fab antibodies for analysis. In this case, sonications were performed in 2 ml of buffer.

The soluble heterodimers prepared above were assayed by ELISA where applicable as described in Example 6.

6. Characterization of Soluble Semisynthetic Fab Heterodimers

A. ELISA

Preliminary ELISA assays were performed to first characterize the binding specificity of the panned phage semisynthetic Fab antibodies prepared above toward synthetic haptens. For ELISA, 1 ug/well of the synthetic haptens prepared in Example 5B was separately admixed to individual wells of a microtiter plate and maintained at 4C overnight to allow the hapten solution to adhere to the walls of the well. After the maintenance period, the wells were washed once with PBS and thereafter maintained with a solution of 3% BSA to block nonspecific sites on the wells. The plates were maintained at 37C for 1 hour after which time the plates were inverted and shaken to remove the BSA solution. Soluble Fab heterodimers expressing the semisynthetic Fab heterodimers prepared in Example 5C were then admixed separately to each well and maintained at 37C for 1 hour to form a immunoreaction products. Following the maintenance period, the wells were washed 10 times with PBS to remove unbound soluble antibody and then maintained with a secondary goat anti-human FAB conjugated to alkaline phosphatase diluted in PBS containing 1% BSA. The wells were maintained at 37C for 1 hour after which the wells were washed 10 times with PBS followed by development with p-nitrophenyl phosphate.

Following 5 rounds of selection as described in Example 5B and conversion of the phagemid from surface display form to soluble antibody producing form, 20 of 20 clones selected for binding the fluorescein conjugate (1), 18 of 20 selected for binding conjugate S-BSA (2) and 1 of 20 selected for binding conjugate C-BSA (3) were positive in ELISA analysis. All clones from F22-derived libraries were also positive following selection for binding to conjugate 1.

Figure 2:
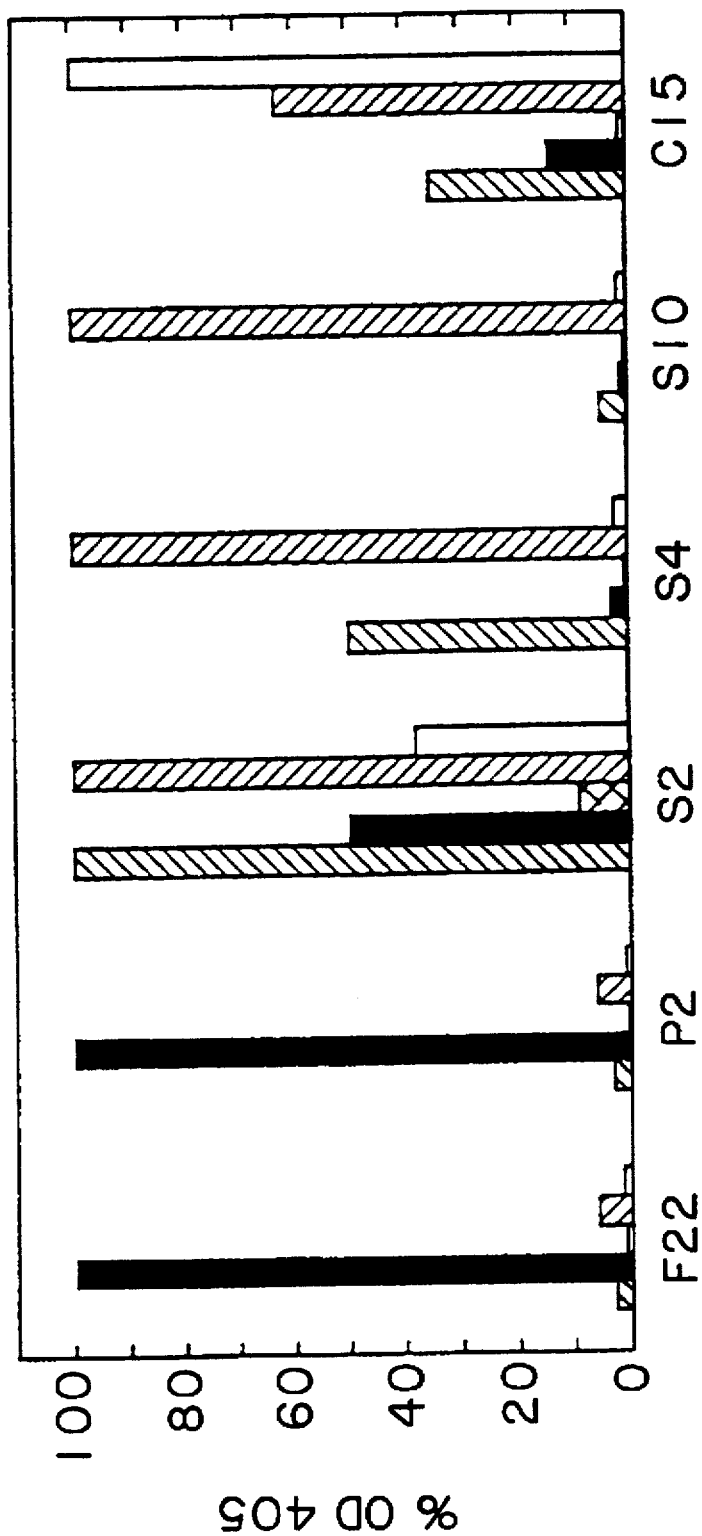
FIG. 2 graphically depicts the anti-synthetic hapten conjugate specificity of selected Fab heterodimers by ELISA. The antigens used in the ELISA shown from left to right are the original pC3AP313-specific tetanus toxoid (forward slashed bar), F1-BSA conjugate (black bar), BSA (horizontal bar), S-BSA conjugate (backward slashed bar) and C-BSA conjugate (white bar). Standard ELISA was performed as described in Example 6A.

Cross reactivities of purified clones were examined by ELISA and are shown in FIG. 2. The antigens used in the ELISA shown from left to right in FIG. 2 are the original pC3AP313-specific tetanus toxoid (forward slashed bar), F1-BSA conjugate (black bar), BSA (horizontal bar), S-BSA conjugate (backward slashed bar) and C-BSA conjugate (white bar). Clones F22, P2, S4, and S10 were specific for the conjugate on which they were selected. Clone S4 retained some reactivity to the parent antigen tetanus toxoid. Clones S2 and C15 were more promiscuous in binding. Selection against binding to BSA was effective as indicated by the limited reactivity of the Fab to this antigen.

B. Affinity Characterization

The affinities of several purified clones were examined by surface plasmon resonance. Only observed monomeric Fab as judged by gel filtration has been observed in contrast to a recent report of single-chain antibody dimerization as described by Griffiths et al., $EMBO$ $J.$, 12:725–734 (1993). The determination of on and off affinity constants, respectively, $k_{on}$ and $k_{off}$ for selected clones were performed using the Biacore instrument from Pharmacia Biosensor (Piscataway, N.J., according to manufacturer's instructions. The F1-BSA conjugate was immobilized in 10 Mm acetate buffer at Ph 2.5 to yield 600 resonance units on a CM5 Biacore sensor chip. The $k_{on}$ and $k_{off}$ were determined by standard analysis in PBS at flow rates of 5 and 8 ul/minutes, respectively as described by Altschun et al., $Biochem.$, 31:6298–6304 (1992).

A compilation of kinetic and equilibrium constants is given in Table I. All Kd's approached the nanomolar range. Clone P2 which was strongly selected from F22 derived libraries had a slightly lower affinity than the parent clone. The affinity of F22 for F1-BSA conjugate by surface plasmon resonance is in close agreement with affinity as determined by competitive analysis.

TABLE 1

| Clone | $k_{on}$ (M$^{-1}$s$^{-1}$) | $k_{off}$ (s$^{-1}$) | $K_a$ (M$^{-1}$) | Kd (nM) |
|---|---|---|---|---|
| F22 | $6.4 \times 10^5$ | $2.2 \times 10^{-2}$ | $2.9 \times 10^7$ | 34 |
| P2 | $2.0 \times 10^5$ | $1.6 \times 10^{-2}$ | $1.3 \times 10^7$ | 80 |
| S2 | $2.8 \times 10^5$ | $8.0 \times 10^{-3}$ | $3.5 \times 10^7$ | 29 |
| S4 | $4.0 \times 10^5$ | $2.2 \times 10^{-2}$ | $1.8 \times 10^7$ | 56 |
| S10 | $3.5 \times 10^5$ | $1.3 \times 10^{-2}$ | $2.7 \times 10^7$ | 37 |

C. Sequence Determination of the Binding Site Proteins

Nucleic acid sequencing was performed on double-stranded DNA using Sequenase 1.0 (USB, Cleveland, Ohio) encoding the specific soluble synthetic hapten-binding Fab heterodimers of this invention characterized above.

The sequences of the CDR3 regions from the selected antibodies are shown in Table 2 and 3. On the left hand side of both tables, the selected antibodies (referred to as the clone) and the anti-hapten conjugate number, 1, 2 or 3, on which the antibody was screened, are listed. The next column from left to right shown is either the amino acid residue sequence of the heavy (HCDR3 in Table 2) and light chain CDR3 (LCDR3 in Table 3) from the designated clone. The SEQ ID Nos are listed adjacent to each of the heavy and light chain sequences. The last column in each table shows the designation of the crossed light and heavy chain library from which the clone was derived and selected. In all cases, the light chain is listed first followed by the heavy chain library or none if applicable.

TABLE 2

| Clone/Conjugate | HCDR3 | SEQ ID NO | Library |
|---|---|---|---|
| FL3/1 | GWSRWSGLDW | 32 | K10/F |
| FL18/1 | SSTKIMRLDT | 33 | K9/F |
| FL19/1 | GMFRRGFYDR | 34 | F |
| FL12/1 | GVRNNFGRWHWVWDS | 35 | E |
| FL13/1 | GRAVRGSRKRVLGYDR | 36 | E |
| FL15 + 1/1 | GRPGVVRRRIAPRMDI | 37 | K9/E |
| FL17/1 | GPKGVFPRWGMASFDR | 38 | K10/E |
| F22/1 | GVNLFRVRNSRPHLDM | 39 | 16 |
| P2/1 | GVNLFRVRNSRPHLDM | 39 | K9/F22 |
| P3/1 | GVNLFRVRNSRPHLDM | 39 | K9/F22 |
| P4/1 | GVNLFRVRNSRPHLDM | 39 | K9/F22 |
| P5/1 | GVNLFRVRNSRPHLDM | 39 | K10/F22 |
| P6/1 | GVNLFRVRNSRPHLDM | 39 | K10/F22 |
| P7/1 | GVNLFRVRNSRPHLDM | 39 | K10/F22 |
|  | GVNLFRVRNSRPHLDM | 39 | K10/F22 |
| S4/2 | GLRGSRGFDR | 40 | K10/F |
| S10/2 | GSWLRGPYDM | 41 |  |
| S12/2 | GTLGEGGYDR | 42 | K10/F |
| S2/2 | GWRSSRGVVWVFSGDA | 43 | K10/E |
| C13/3 | GDWGWFTRVATWRPDV | 44 | K10/E |

TABLE 3

| Clone/Conjugate | LCDR3 | SEQ ID NO | Library |
|---|---|---|---|
| FL3/1 | QQYLPGGRYT | 45 | K10/F |
| FL18/1 | QQYRVEGQT | 46 | K9/F |
| FL19/1 | QQYGGSPW | 47 | F |
| FL12/1 | QQYGGSPW | 47 | E |
| FL13/1 | QQYGGSPW | 47 | E |
| FL15 + 1/1 | QQYSRHRFT | 48 | K9/E |
| FL17/1 | QQYRYPLIWT | 49 | K10/E |
| F22/1 | QQYGSSLWT | 50 | 16 |
| P2/1 | QQYTRPGVT | 51 | K9/F22 |

TABLE 3-continued

| Clone/Conjugate | LCDR3 | SEQ ID NO | Library |
|---|---|---|---|
| P3/1 | QQYSFKNWT | 52 | K9/F22 |
| P4/1 | QQYGYRKWT | 53 | K9/F22 |
| P5/1 | QQYTPRRGAT | 54 | K10/F22 |
| P6/1 | QQYTPRVGHT | 55 | K10/F22 |
| P7/1 | QQYKYGRGMT | 56 | K10/F22 |
|  | QQYKYGRGMT | 56 | K10/F22 |
| S4/2 | QQYGKKQWT | 57 | K10/F |
| S10/2 | QQYVRRSGT | 58 |  |
| S12/2 | QQYGKRSPVT | 59 | K10/F |
| S2/2 | QQYARATGLT | 60 | K10/E |
| C13/3 | QQYSRFVSRT | 61 | K10/E |

A number of features are immediately obvious from looking at the amino acid residue sequence of the selected clones, the libraries from which they were derived and the synthetic hapten on which they were selected. No clones derived from libraries containing HCDR3 length of 5 survived the competitive selection. Furthermore, no clones derived from libraries with only light chain variation were selected. All clones were derived from heavy chain libraries where the first and penultimate residues have been fixed as Gly and Asp, respectively. Clone FL18 contained a serine (S) at the first position that is likely an artifact of the synthesis and assembly and is the result of a single base change (GGT to AGT). This has been noted in previous examinations of libraries E and F. These results indicate that completeness of a semisynthetic Fab library does not necessarily correlate with the quality of antibodies which can be derived from it. Libraries K8, CDR3-HC5, and G all contained sufficient members to be judged as 99% complete and yet no clones from these libraries survived the competitive selection. Indeed most clones were derived from the crossed libraries that were the most incomplete but probably most structurally diverse. These results highlight the fact that an evolved combining site is under remodeling which may be best achieved with more extensive mutation rather than less. This argument may explain the low affinity clones isolated by the randomization of 5 residues reported previously by Hoogenboom et al., *J. Mol. Biol.*, 227:381–388 (1992).

There is evidence for selection of consensus sequence in the clones. For example, in the eighth position of HCDR3 of clones S4, S10, and S12 is an aromatic residue. Their corresponding light chains contain the basic doublets KK, RR, and KR, respectively. Furthermore, sequence similarity is noted in clones S4 and S2 which differ in length but contain very similar carboxy-terminal HCDR3 regions. Clone S10 and S2 were found 3 and 2 times, respectively, identical at the nucleotide level following sequencing of 7 clones.

Examination of the role of LCDR3 in the previously selected clone F22 revealed that considerably different sequence may be tolerated in this region as compared to the starting clone. The predominant clone was P2 that was found 5 times identical at amino acid level among the 10 clones sequenced. This clone was found to be encoded by 4 unique nucleotide sequences. Naturally occurring murine and human kappa light chain CDR3 regions show a strong conservation of Pro at Kabat position 95. None of the clones derived from the semisynthetic libraries contain proline (P) at this position. This indicates that proline is conserved for something other than structural reasons or there is editing of this sequence at some level.

Thus, a variety of anti-hapten semisynthetic Fab antibodies can be directly selected from semisynthetic antibody libraries derived from the randomization of 1 or 2 CDR regions, specifically in the heavy and light chain CDR3. Like naturally occurring antibodies, semisynthetic antibodies exhibited differing degrees of cross-reactivity. Libraries with greater structural diversity, those with more residues randomized, were functionally superior over complete but structurally limited libraries. However, constraining diversity in the heavy chain CDR3 to the extent of holding the penultimate position fixed as aspartic acid improved the quality of the library and highlights the structural role of this residue. No such phenomena has yet to be observed in the light chain CDR3 though 4 positions in this region have yet to be examined.

7. Preparation of a Dicistronic Expression Vector Library Capable of Expressing a Phagemid Fab Display Protein Derived From Human Anti-Thyroid Peroxidase Antibody Light and Heavy Chain Libraries:

A. Preparation of Lymphocyte MRNA

Thyroid tissue was obtained from a patient with Hashimoto's thyroiditis containing anti-thyroid peroxidase antibodies, and thyroid lymphocytes were isolated from the thyroid tissue, as described in Atherton et al., *Immunology*, 55:271–279 (1985). RNA was then extracted from the freshly isolated cells (Hexham et al., *Autoimmunity*, 12:135–141 (1992) and Hexham et al., *Autoimmunity*, 14:169–172 (1992)). Analysis of the Hashimoto's patient serum by ELISA (Schardt et al., *J. Immunol. Methods*, 55:155–168 (1982)) at the time of the operation indicated the presence of high levels of thyroid peroxidase (TPO) autoantibodies, primarily of the IgG/kappa type.

B. Construction of Heavy and Light Chain Thyroid Peroxidase Antibody Libraries in Lambda Phage Heavy and light chain thyroid peroxidase antibody libraries were first constructed in lambda phage as described in Hexham et al., *Autoimmunity*, 12:135–141 (1992), using the lymphocyte mRNA isolated in Example 7A. The heavy and light chain lambda phage libraries were converted to phagemid libraries through an in vivo excision process (Short et al., supra) using interference resistant M13 helper phage VCSM13 (Stratagene, La Jolla, Calif.).

Following the excision of the lambda phage library encoding the light chain, eleven clones were randomly chosen for further analysis. DNA was isolated and the nucleotide sequence determined by the dideoxy chain-termination method (Sanger et al., *Proc. Natl. Acad. Sci. U.S.A.*, 74:5463–5467 (1977)) using Sequenase 2.0 (United States Biochem).

C. Construction of Heavy and Light Chain Thyroid Peroxidase Antibody Libraries in Pcomb3

The heavy and light chain antibody encoding sequences identified in Example 7B were removed from the excised phagemid vector and inserted into the monovalent Fab phage display vector, Pcomb3. The heavy and light chain sequences were respectively isolated by restriction digestion with Xho I/Spe I and Sac i/Xba I and ligated into a similarly digested Pcomb3 vector. The ligation procedure in creating expression vector libraries was performed as described in Example 2. The primary library contained $10^5$ independent clones. Twelve clones were selected at random and analyzed by restriction digestion of the DNA with Not I. 83% of the clones examined contained the 2.5 kb insert fragment consistent with an Fab-containing vector.

8. Selection of Anti-Thyroid Peroxidase Fab Antibodies Expressed on Phage

A. Preparation of Phage Expressing Fab Heterodimers

Phage expressing Fabs reactive with thyroid peroxidase (TPO) were prepared as described in Example 2 using the expression vector library produced in Example 7C to form a phage library containing phage with Fab display protein.

B. Selection of the Phagemid-Displayed Fab Heterodimers

1) Multiple Pannings of the Phage Library Having Phagemid Fab-Displayed Binding Site Proteins The phage library prepared in Example 8A was panned as described in Example 5B1 on microtiter plates coated with TPO target molecules to isolate phagemid displaying anti-TPO Fab heterodimers. Consecutive rounds of panning on TPO-coated ELISA plates resulted in an enrichment of approximately $10^4$-fold. Round 1 of panning gave a recovery of $2 \times 10^3$ colony forming units (cfu); round 2 gave a recovery of $3.2 \times 10^3$ cfu; round 3 gave a recovery of $>10^6$ cfu; and round 4 gave a recovery of $>10^7$ cfu. The panned phage surface expression clones were then converted into clones expressing soluble Fab antibodies as described in Example 5C for further characterization.

9. Characterization of Soluble Fab Heterodimers

A. ELISA

ELISA assays were performed to characterize the binding specificity of individual panned phage Fab antibodies with TPO. ELISA was conducted as described in Example 6A with TPO instead of the synthetic haptens as the target molecule and the Fab was detected with anti-human IgG (Fab) conjugated to alkaline phosphatase (Sigma, St. Louis, Mo.).

Following 4 rounds of selection as described in Example 8B1 and conversion of the phagemid form from surface display form to soluble antibody producing form, 17 of 24 clones selected for binding to TPO were positive in the ELISA analysis. Cross reactivities of purified clones with irrelevant proteins were examined by ELISA as described in Example 6A. The antigens used in the ELISA were a range of concentrations of human TPO, human thyroglobulin (RSR Ltd, Cardiff, CF2 7HE), human myeloperoxidase (Sigma, St. Louis, Mo.), and bovine lactoperoxidase (Sigma, St. Louis, Mo.). Binding of the Fabs to TPO-coated plates was inhibited by human TPO, however, no inhibition was observed with human thyroglobulin (up to 100 Nm), human myeloperoxidase (up to 200 Nm), or bovine lactoperoxidase (up to 10 µM).

B. Affinity Characterization

The affinities of several purified clones were estimated by inhibition ELISA with various concentrations of TPO as the competitor. The affinity constants of 6F, 7F, and 10I, were estimated to be $8.0 \times 10^8$, $8.0 \times 10^8$, and $0.3 \times 10^9$ M$^{-1}$, respectively.

Thus, three diverse, novel, high-affinity (approximately $10^{-9}$ M$^{-1}$) anti-TPO Fab antibodies were directly selected from a Pcomb3 phage display combinatorial library. These Fabs, designated 6F, 7F, and 10I, were obtained with a relative frequency of 12:4:1 from an enriched population of phage with Fab 10I having the highest affinity for TPO.

C. Sequence Determination of the Binding Site Proteins

The nucleotide sequence of the specific soluble TPO-binding Fab heterodimers of this invention was determined. The nucleotide sequence of the anti-TPO monoclonal antibody 2G4 (Horimoto et al., *Autoimmunity*, 14:1–7 (1992) and Hexham, et al., *Autoimmunity*, 14:169–172 (1992)) and the SP series of recombinant anti-TPO antibodies (Portolano et al., *Biochem. Biophys. Res. Comm.*, 179:372–377 (1991), Portolano et al., *J. Clin. Invest.*, 90:720–726 (1992), and Portolano et al., *J. Immunol.*, 150:880–887 (1993)) was also determined. Nucleic acid sequencing was performed on double-stranded DNA using Sequenase 2.0 (USB, Cleveland, Ohio). The primers SEQGb, SEQKb, and the M13 reverse primer were used as described in Hexham et al., *Autoimmunity*, 12:135–141 (1992).

Sequence analysis and database searches were carried out using the SERC Seqnet facility on a Silicon Graphics Crimson running the GCG suite of programs (Devereux, et al., *Nucl. Acids Res.*, 12:387–395 (1984)). Variable region sequences were identified and analyzed using the FASTA program to search the Genbank and EMBL databases and by direct comparison with known sequences (Kabat et al., supra).

The sequences of the CDR regions from anti-TPO antibodies are shown in Tables 4 and 5. On the left hand side of both tables, the anti-TPO antibodies (referred to as the clone) are listed. The next column from left to right shown is either the amino acid residue sequence of the heavy CDRs (HCDR in Table 4) and light chain CDRs (LCDR in Table 5) from the designated clone. The SEQ ID NOs corresponding to the complete amino acid residue sequence as listed in the Sequence Listing are listed adjacent to each of the heavy and light chain amino acid sequences in Tables 4 and 5.

with the vk01/012 germline gene. Two other anti-TPO antibodies (2G4 and 7F) use light chain genes which show greatest homology, 87 and 97%, respectively, to the kv325 germline gene (Radoux et al., *J. Exp. Med.*, 164:2119–2124 (1986)). The kv325 germline gene is also described in this invention as a universal light chain and is the light chain sequence given in SEQ ID NO 2.

To address the question of bias in the light chain representation in the thyroid peroxidase antibody library, eleven clones were randomly selected from the library before antigen selection and the nucleotide sequence determined. The data indicates that all eleven light chain sequences are different from each other and from the anti-TPO Fab light chain amino acid residue sequences. The eleven clones were derived from three different kappa gene families, indicating a diverse library. Analysis of the eleven sequences revealed that 2 (1%) used vk02/012 and that 4 (36%) used kv325 which are similar frequencies to those obtained in the anti-gp120 antibodies also described herein. Given that the vk02/012 and kv325 genes constitute only 3 out of the 45–50 germline kappa genes, it appears that these genes are present at a higher than expected frequency in the unselected library. This could be due to bias introduced by the design of the PCR primers, however, the vk02/012 germline light chain is also represented strongly in the SP series of anti-TPO antibodies which were derived using different PCR primers. In addition, the vk02/012 and kv325 light chains are frequently represented in human hybridoma derived antibodies against several non-self antigens. This could be interpreted as an over representation of the vk02/012 and kv325 light chains in antibody-producing cells in both normal and autoimmune cells.

The native light chains of two of the antibodies, 6F and 10I, use the same germline Vkappa gene, vk02/012, as do the SP family of anti-TPO autoantibodies. The vk02/012

TABLE 4

| Clone | HCDR1 | HCDR2 | HCDR3 | SEQ ID NO |
|---|---|---|---|---|
| 10I | SYAMT | SPSANGDFAYYADSVKG | AGRILGVVLWYSLYYGFDV | 63 |
| 6F | SHDIN | WIINRGTTSRYAQKFQG | GAGAGGTW | 64 |
| SP1.2 | GHYMH | WISPNRGATRFAQKFQG | TRIAYYGMDV | 65 |

TABLE 5

| Clone | LCDR1 | LCDR2 | LCDR3 | SEQ ID NO |
|---|---|---|---|---|
| 10I | RASSNISSYIN | AASSLQS | QQSYSTPFT | 66 |
| 6F | RASQRISSYIN | AASSLQS | QQSYSTPYT | 67 |
| SP1.2 | RASENISSYIN | AASTLQS | QQTYSSPFT | 68 |
| SP1.4 | RASQTIGTYIN | TASTLQS | QQSYSTPWT | 69 |
| SP1.5 | RASQNIGKYIN | GTSTLQS | QQSYSTPWT | 70 |

Analysis of the nucleotide and deduced amino acid sequences of the HC and LC variable regions of 6F, 7F, and 10I allows most of the Vkappa VH, JH, Kkappa, and DH genes to be assigned to the germline gene from which they were derived. A striking feature of these antibodies is that five of them (6F, 10I, and the three SP antibodies shown) appear to have VkappaI light chains encoded by the same vk02 or vk012 germline gene (Pargent et al., *Eur. J. Immunol.*, 21:1821–1827 (1991)). Vk02 has a coding region which is indistinguishable from that of vk012 and therefore the assignment of the antibody light chains to either germline gene is equally valid. The light chains of 6F and 10I share 98.9% and 99.6% nucleotide identity, respectively, gene is also expressed in several other autoantibodies including acetylcholine receptor autoantibodies and rheumatoid factors.

Light and heavy chain pairs derived from hybridomas represent an in vivo pairing while recombinant antibodies produced as described herein may represent both the in vivo and in vitro pairings. To determine the frequency of occurrence of the vk02/012 and vk325 light chains in known light chain sequences, the nucleotide sequence database was searched with the germline variable region encoding sections of vk02/012 and vk325. Five out of seven human hybridoma antibodies of known specificity which contain the kv02/012 light chain were autoantibodies. Nineteen out of 24 antibodies with the kv325 light chain of known specificity recognized were autoantibodies. The hybridoma antibodies against non-self antigens displayed a wide range of specificities, including Haemophilus influenzae (kv02/012), hepatitis B virus (kv02/012), Neisseria meningitides (kv325), human cytomegalovirus (kv325), and HIV (kv325). Thus, in vivo pairings, as represented by hybridoma antibodies, also contain a high frequency of the kv02/012 and kv325 light chain. Further, in a diverse, non-antigen selected sample of 34 kappa light chain genes, amplified from peripheral blood lymphocytes by PCR (Marks et al., *Eur. J. Immunol.*, 21:985–991 (1991)), vk02/012 was represented four times. In previous studies on murine responses against the hapten NPN and in the human response against HIV-1 gp120 protein, considerable promiscuity of pairing of light chains with a particular heavy chain has been observed. Taken together, and given the over representation of autoantibodies in the database, these results indicate that expression of the k02/012 light chain gene is high, not only in autoimmune but also in normal immune responses. The vk02/012 may therefore be a much-used "plastic" light chain, or a "universal" light chain, which can combine with different heavy chains where specificity is dictated by the heavy chain.

The native light chain in the pC3AP313 phagemid expression vector that binds to tetanus toxoid, kv325, has been identified in antibodies against foreign antigens such as cytomegalovirus and digoxin. With the methodology of repertoire cloning and sequencing, the pC3AP313 light chain has been observed with a high frequency. For example, the light chain was found in the unmutated gene in an antibody binding hepatitis B surface antigen and was slightly mutated in an anti-thyroglobulin antibody. Comparison of 33 antibodies binding to HIV-1 surface glycoprotein gp120 showed that no less than 13 of the antibodies had the pC3AP313 light chain as the closest light chain germline gene.

Thus, the native pC3AP313 light chain and native 6F light chain, have been coined universal light chains due to their high representation in Fab antibody heterodimers obtained through repertoire cloning. The pC3AP313 and 6F light chains are the human germ-line genes Humkv325 and Humkv02/012, respectively, and behave as a universal light chain V region in combination with various J regions in pairing with a wide range of different heavy chain Fab fragments. The light chains thus exhibit plastic behavior in that if in combination with heavy chains that bind to a wide variety of antigens, the specificity and affinity is not abrogated by the presence of the universal light chain. The amino acid residue light chain sequence is unique in this respect and therefore plays an important role in the utility of recombinant antibody libraries from natural and synthetic sources.

The ability to produce human anti-hapten antibodies that have either the native pC3AP313 encoded universal light chain sequence or further randomized to improve the specificity and affinity of the heterodimer binding may be significant in the development of catalytic antibodies as pharmaceuticals. Moreover, the ability to generate unique crossed libraries having native/native heavy and light chain CDR domains, native heavy and randomized light chain CDR domains, randomized heavy and native light chain CDR domains, and finally both randomized heavy and light chain CDR domains is a valuable methodology provided by this invention to create new and improved Fab heterodimers with new or improved specificities and affinities through expression of selected clones from the libraries.

10. Deposit of Materials

The following plasmid was deposited on or before Feb. 2, 1993, with the American Type Culture Collection, 1301 Parklawn Drive, Rockville, Md., USA (ATCC):

| Material | ATCC Accession No. |
| --- | --- |
| Plasmid pC3AP313 | ATCC 75408 |

This deposits was made under the provisions of the Budapest Treaty on the International Recognition of the Deposit of Microorganisms for the Purpose of Patent Procedure and the Regulations thereunder (Budapest Treaty). This assures maintenance of a viable plasmid deposit for 30 years from the date of deposit. The deposit will be made available by ATCC under the terms of the Budapest Treaty which assures permanent and unrestricted availability of the progeny of the viable plasmids to the public upon issuance of the pertinent U.S. patent or upon laying open to the public of any U.S. or foreign patent application, whichever comes first, and assures availability of the progeny Go one determined by the U.S. Commissioner of Patents and Trademarks to be entitled thereto according to 35 U.S.C. §122 and the Commissioner's rules pursuant thereto (including 37 CFR §1.14 with particular reference to 886 OG 638). The assignee of the present application has agreed that if the plasmid deposit should die or be lost or destroyed when cultivated under suitable conditions, it will be promptly replaced on notification with a viable specimen of the same plasmid. Availability of the deposited plasmid is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the plasmid deposited, since the deposited embodiment is intended as a single illustration of one aspect of the invention and any plasmid vectors that are functionally equivalent are within the scope of this invention. The deposit of material does not constitute an admission that the written description herein contained is inadequate to enable the practice of any aspect of the invention, including the best mode thereof, nor is it to be construed as limiting the scope of the claims to the specific illustration that it represents. Indeed, various modifications of the invention in addition to those shown and described herein will become apparent to those skilled in the art from the foregoing description and fall within the scope of the appended claims.

What is claimed is:

1. A method for producing a heterodimeric immunoglobulin molecule having immunoglobulin variable domain heavy and light chain polypeptides comprising the steps of:

a) combining an immunoglobulin variable domain light chain gene that includes a sequence having the sequence of the light chain shown in SEQ ID NO 2 with one or more immunoglobulin variable domain heavy chain genes to form a combinatorial immunoglobulin heavy and light chain gene library, said combining comprising operatively linking said light chain gene with one of said heavy chain genes in a vector capable of co-expression of said heavy and light chain genes;

b) expressing the combinatorial gene library to form a combinatorial antibody library of expressed heavy and light chain polypeptides; and c) selecting species of said combinatorial antibody library for the ability to bind a preselected antigen.

2. The method of claim 1 wherein said immunoglobulin light chain gene has the sequence of the light chain gene in ATCC Accession No. 75408.

3. The method of claim 1 wherein said one or more immunoglobulin heavy chain genes is a library of heavy chain genes.

* * * * *

SEQUENCE LISTING ( 1 ) GENERAL INFORMATION:

( i i i ) NUMBER OF SEQUENCES: 70

( 2 ) INFORMATION FOR SEQ ID NO:1:

( i ) SEQUENCE CHARACTERISTICS:

( A ) LENGTH: 687 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:1:

| | | | | | | |
|---|---|---|---|---|---|---|
| CTCGAGCAGT | CTGGGGCTGA | GGTGAAGAAG | CCTGGGTCCT | CGGTGAAGGT | CTCCTGCAGG | 60 |
| GCTTCTGGAG | GCACCTTCAA | CAATTATGCC | ATCAGCTGGG | TGCGACAGGC | CCCTGGACAA | 120 |
| GGGCTTGAGT | GGATGGGAGG | GATCTTCCCT | TTCCGTAATA | CAGCAAAGTA | CGCACAACAC | 180 |
| TTCCAGGGCA | GAGTCACCAT | TACCGCGGAC | GAATCCACGG | GCACAGCCTA | CATGGAGCTG | 240 |
| AGCAGCCTGA | GATCTGAGGA | CACGGCCATA | TATTATTGTG | CGAGAGGGGA | TACGATTTTT | 300 |
| GGAGTGACCA | TGGGATACTA | CGCTATGGAC | GTCTGGGGCC | AAGGGACCAC | GGTCACCGTC | 360 |
| TCCGCAGCCT | CCACCAAGGG | CCCATCGGTC | TTCCCCCTGG | CACCCTCCTC | CAAGAGCACC | 420 |
| TCTGGGGGCA | CAGCGGCCCT | GGGCTGCCTG | GTCAAGGACT | ACTTCCCCGA | ACCGGTGACG | 480 |
| GTGTCGTGGA | ACTCAGGCGC | CCTGACCAGC | GGCGTGCACA | CCTTCCCGGC | TGTCCTACAG | 540 |
| TCCTCAGGAC | TCTACTCCCT | CAGCAGCGTG | GTGACCGTGC | CCTCCAGCAG | CTTGGGCACC | 600 |
| CAGACCTACA | TCTGCAACGT | GAATCACAAG | CCCAGCAACA | CCAAGGTGGA | CAAGAAAGCA | 660 |
| GAGCCCAAAT | CTTGTGACAA | AACTAGT | | | | 687 |

( 2 ) INFORMATION FOR SEQ ID NO:2:

( i ) SEQUENCE CHARACTERISTICS:
        ( A ) LENGTH: 646 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:2:

| | | | | | | |
|---|---|---|---|---|---|---|
| GAGCTCACGC | AGTCTCCAGG | CACCCTGTCT | TTGTCTCCAG | GGGAAAGAGC | CACCCTCTCC | 60 |
| TGCAGGGCCA | GTCACAGTGT | TAGCAGGGCC | TACTTAGCCT | GGTACCAGCA | GAAACCTGGC | 120 |
| CAGGCTCCCA | GGCTCCTCAT | CTATGGTACA | TCCAGCAGGG | CCACTGGCAT | CCCAGACAGG | 180 |
| TCCAGTGGCA | GTGGGTCTGG | GACAGACTTC | ACTCTCACCA | TCAGCAGACT | GGAGCCTGAA | 240 |
| GATTTTGCAG | TGTACTACTG | TCAGCAGTAT | GGTGGCTCAC | CGTGGTTCGG | CCAAGGGACC | 300 |
| AAGGTGGAAC | TCAAACGAAC | TGTGGCTGCA | CCATCTGTCT | TCATCTTCCC | GCCATCTGAT | 360 |
| GAGCAGTTGA | AATCTGGAAC | TGCCTCTGTT | GTGTGCCTGC | TGAATAACTT | CTATCCCAGA | 420 |
| GAGGCCAAAG | TACAGTGGAA | GGTGGATAAC | GCCCTCCAAT | CGGGTAACTC | CCAGGAGAGT | 480 |
| GTCACAGAGC | AGGACAGCAA | GGACAGCACC | TACAGCCTCA | GCAGCACCCT | GACGCTGAGC | 540 |
| AAAGCAGACT | ACGAGAAACA | CAAAGTCTAC | GCCTGCGAAG | TCACCCATCA | GGGCCTGAGT | 600 |
| TCGCCCGTCA | CAAAGAGCTT | CAACAGGGGA | GAGTGTTAAT | TCTAGA | | 646 |

( 2 ) INFORMATION FOR SEQ ID NO:3:

( i ) SEQUENCE CHARACTERISTICS:

(A) LENGTH: 21 base pairs
         (B) TYPE: nucleic acid
         (C) STRANDEDNESS: single
         (D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:3:

GAATTCTAAA CTAGCTAGTC G                                                       21

(2) INFORMATION FOR SEQ ID NO:4:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:4:

ATACTGCTGA CAGTAATACA C                                                       21

(2) INFORMATION FOR SEQ ID NO:5:

(i) SEQUENCE CHARACTERISTICS:
         (A) LENGTH: 57 base pairs
         (B) TYPE: nucleic acid
         (C) STRANDEDNESS: single
         (D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:5:

TATTACTGTC AGCAGTATNN KNNKNNKNNK ACTTTCGGCG GAGGGACCAA GGTGGAG                57

(2) INFORMATION FOR SEQ ID NO:6:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:6:

AATACGACTC ACTATAGGGC G                                                       21

(2) INFORMATION FOR SEQ ID NO:7:

(i) SEQUENCE CHARACTERISTICS:
         (A) LENGTH: 48 base pairs
         (B) TYPE: nucleic acid
         (C) STRANDEDNESS: single
         (D) TOPOLOGY: linear (  i i  ) MOLECULE TYPE: cDNA ( i i i ) HYPOTHETICAL: NO ( i v ) ANTI-SENSE: NO ( x i ) SEQUENCE DESCRIPTION: SEQ ID NO:7:

TATTACTGTC AGCAGTATNN KNNKNNKNNK ACTTTCGGCG GAGGGACC 48

( 2 ) INFORMATION FOR SEQ ID NO:8:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:8:

TATTACTGTC AGCAGTATNN KNNKNNKNNK NNKACTTTCG GCGGAGGGAC CAAGGTGGAG 60

( 2 ) INFORMATION FOR SEQ ID NO:9:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:9:

TATTACTGTC AGCAGTATNN KNNKNNKNNK NNKACTTTCG GCGGAGGGAC C 51

( 2 ) INFORMATION FOR SEQ ID NO:10:

( i ) SEQUENCE CHARACTERISTICS:
        ( A ) LENGTH: 75 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:10:

GATTTGCAG TGTATTACTG TCAGCAGTAT NNKNNKNNKN NKNNKNNKAC TTTCGGCGGA 60

GGGACCAAGG TGGAG 75

( 2 ) INFORMATION FOR SEQ ID NO:11:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:11:

TATTACTGTC AGCAGTATNN KNNKNNKNNK NNKNNKACTT TCGGCGGAGG GACC    54

( 2 ) INFORMATION FOR SEQ ID NO:12:

( i ) SEQUENCE CHARACTERISTICS:
        ( A ) LENGTH: 75 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:12:

GATTTTGCAG TGTATTACTG TNNKNNKNNK NNKNNKNNKN NKNNKNNKNN KTTCGGCGGA    60

GGGACCAAGG TGGAG    75

( 2 ) INFORMATION FOR SEQ ID NO:13:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:13:

GTTCCACCTT GGTCCCTTGG CCGAAMNNMN NMNNMNNMNN MNNMNNMNNA CAGTAGTACA    60

CTGCAAAATC    70

( 2 ) INFORMATION FOR SEQ ID NO:14:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:14:

GTTCCACCTT GGTCCCTTGG CCGAAMNNMN NMNNMNNMNN MNNMNNMNNM NNMNNACAGT    60

AGTACACTGC AAAATC    76

( 2 ) INFORMATION FOR SEQ ID NO:15:

( i ) SEQUENCE CHARACTERISTICS:
        ( A ) LENGTH: 94 base pairs
        ( B ) TYPE: nucleic acid
        ( C ) STRANDEDNESS: single
        ( D ) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:15:

GTTCCACCTT GGTCCCTTGG CCGAAMNNMN NMNNMNNMNN MNNMNNMNNM NNMNNMNNMN   60

NMNNMNNMNN MNNACAGTAG TACACTGCAA AATC   94

(2) INFORMATION FOR SEQ ID NO:16:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:16:

TTCGGCCAAG GGACCAAGGT GGAAC   25

(2) INFORMATION FOR SEQ ID NO:17:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:17:

GCAATTAACC CTCACTAAAG GG   22

(2) INFORMATION FOR SEQ ID NO:18:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:18:

TCTCGCACAG TAATACACGG CCGT   24

(2) INFORMATION FOR SEQ ID NO:19:

(i) SEQUENCE CHARACTERISTICS:
      (A) LENGTH: 57 base pairs
      (B) TYPE: nucleic acid
      (C) STRANDEDNESS: single
      (D) TOPOLOGY: linear (i i) MOLECULE TYPE: cDNA (iii) HYPOTHETICAL: NO (iv) ANTI-SENSE: NO (xi) SEQUENCE DESCRIPTION: SEQ ID NO:19:

GCCGTGTATT ACTGTGCGAG ANNKNNKNNK GACNNKTGGG GCCAAGGGAC CACGGTC    57

(2) INFORMATION FOR SEQ ID NO:20:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:20:

TTGATATTCA CAAACGAATG G    21

(2) INFORMATION FOR SEQ ID NO:21:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:21:

GCCGTGTATT ACTGTGCGAG AGGTNNKNNK NNKNNKNNKN NKNNKGACNN KTGGGGCCAA    60

GGGACCACGG TC    72

(2) INFORMATION FOR SEQ ID NO:22:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:22:

GCCGTGTATT ACTGTGCGAG AGGTNNKNNK NNKNNKNNKN NKNNKNNKNN KNNKNNKNNK    60

NNKGACNNKT GGGGCCAAGG GACCACGGTC    90

(2) INFORMATION FOR SEQ ID NO:23:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: cDNA ( i i i ) HYPOTHETICAL: NO ( i v ) ANTI-SENSE: NO ( x i ) SEQUENCE DESCRIPTION: SEQ ID NO:23:

GTGTATTATT GTGCGAGANN SNNSNNSNNS NNSTGGGGCC AAGGGACCAC G    51

( 2 ) INFORMATION FOR SEQ ID NO:24:

( i ) SEQUENCE CHARACTERISTICS:
        ( A ) LENGTH: 66 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:24:

GTGTATTATT GTGCGAGANN SNNSNNSNNS NNSNNSNNSN NSNNSNNSTG GGGCCAAGGG    60

ACCACG    66

( 2 ) INFORMATION FOR SEQ ID NO:25:

( i ) SEQUENCE CHARACTERISTICS:
        ( A ) LENGTH: 84 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:25:

GTGTATTATT GTGCGAGANN SNNSNNSNNS NNSNNSNNSN NSNNSNNSNN SNNSNNSNNS    60

NNSNNSTGGG GCCAAGGGAC CACG    84

( 2 ) INFORMATION FOR SEQ ID NO:26:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:26:

TATACTGTCA GCAGTAT    17

( 2 ) INFORMATION FOR SEQ ID NO:27:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA (iii) HYPOTHETICAL: NO (iv) ANTI-SENSE: NO (xi) SEQUENCE DESCRIPTION: SEQ ID NO:27:

GATTTTGCAG TGTATTACTG TCAGCAGTAT 30

(2) INFORMATION FOR SEQ ID NO:28:

(i) SEQUENCE CHARACTERISTICS:
 (A) LENGTH: 27 base pairs
 (B) TYPE: nucleic acid
 (C) STRANDEDNESS: single
 (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:28:

ACTTTCGGCG GAGGGACCAA GGTGGAG 27

(2) INFORMATION FOR SEQ ID NO:29:

(i) SEQUENCE CHARACTERISTICS:
 (A) LENGTH: 18 base pairs
 (B) TYPE: nucleic acid
 (C) STRANDEDNESS: single
 (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:29:

ACTTTCGGCG GAGGGACC 18

(2) INFORMATION FOR SEQ ID NO:30:

(i) SEQUENCE CHARACTERISTICS:
 (A) LENGTH: 25 base pairs
 (B) TYPE: nucleic acid
 (C) STRANDEDNESS: single
 (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:30:

GTTCCACCTT GGTCCCTTGG CCGAA 25

(2) INFORMATION FOR SEQ ID NO:31:

(i) SEQUENCE CHARACTERISTICS:
 (A) LENGTH: 21 base pairs
 (B) TYPE: nucleic acid
 (C) STRANDEDNESS: single
 (D) TOPOLOGY: linear (ii) MOLECULE TYPE: cDNA (iii) HYPOTHETICAL: NO (iv) ANTI-SENSE: NO ( x i ) SEQUENCE DESCRIPTION: SEQ ID NO:31:

ACAGTAGTAC ACTGCAAAAT C                                                        21

( 2 ) INFORMATION FOR SEQ ID NO:32:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: protein ( v ) FRAGMENT TYPE: internal ( x i ) SEQUENCE DESCRIPTION: SEQ ID NO:32:

```
Gly  Trp  Ser  Arg  Trp  Ser  Gly  Leu  Asp  Trp
1                  5                        10
```

( 2 ) INFORMATION FOR SEQ ID NO:33:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: protein ( v ) FRAGMENT TYPE: internal ( x i ) SEQUENCE DESCRIPTION: SEQ ID NO:33:

```
Ser  Ser  Thr  Lys  Ile  Met  Arg  Leu  Asp  Thr
1                  5                        10
```

( 2 ) INFORMATION FOR SEQ ID NO:34:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: protein ( v ) FRAGMENT TYPE: internal ( x i ) SEQUENCE DESCRIPTION: SEQ ID NO:34:

```
Gly  Met  Phe  Arg  Arg  Gly  Phe  Tyr  Asp  Arg
1                  5                        10
```

( 2 ) INFORMATION FOR SEQ ID NO:35:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: protein ( v ) FRAGMENT TYPE: internal ( x i ) SEQUENCE DESCRIPTION: SEQ ID NO:35:

```
Gly  Val  Arg  Asn  Asn  Phe  Gly  Arg  Trp  His  Trp  Val  Trp  Asp  Ser
1                  5                        10                       15
```

( 2 ) INFORMATION FOR SEQ ID NO:36:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: cDNA ( v ) FRAGMENT TYPE: internal ( x i ) SEQUENCE DESCRIPTION: SEQ ID NO:36:

Gly Arg Ala Val Arg Gly Ser Arg Lys Arg Val Leu Gly Tyr Asp Arg
1               5                   10                  15

( 2 ) INFORMATION FOR SEQ ID NO:37:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: protein ( v ) FRAGMENT TYPE: internal ( x i ) SEQUENCE DESCRIPTION: SEQ ID NO:37:

Gly Arg Pro Gly Val Val Arg Arg Arg Ile Ala Pro Arg Met Asp Ile
1               5                   10                  15

( 2 ) INFORMATION FOR SEQ ID NO:38:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: protein ( v ) FRAGMENT TYPE: internal ( x i ) SEQUENCE DESCRIPTION: SEQ ID NO:38:

Gly Pro Lys Gly Val Phe Pro Arg Trp Gly Met Ala Ser Phe Asp Arg
1               5                   10                  15

( 2 ) INFORMATION FOR SEQ ID NO:39:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: protein ( v ) FRAGMENT TYPE: internal ( x i ) SEQUENCE DESCRIPTION: SEQ ID NO:39:

Gly Val Asn Leu Phe Arg Val Arg Asn Ser Arg Pro His Leu Asp Met
1               5                   10                  15

( 2 ) INFORMATION FOR SEQ ID NO:40:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: protein ( v ) FRAGMENT TYPE: internal ( x i ) SEQUENCE DESCRIPTION: SEQ ID NO:40:

Gly Leu Arg Gly Ser Arg Gly Phe Asp Arg
1               5                   10

( 2 ) INFORMATION FOR SEQ ID NO:41:

( i ) SEQUENCE CHARACTERISTICS:
　　( A ) LENGTH: 10 amino acids
　　( B ) TYPE: amino acid
　　( D ) TOPOLOGY: linear ( i i ) MOLECULE TYPE: protein ( v ) FRAGMENT TYPE: internal ( x i ) SEQUENCE DESCRIPTION: SEQ ID NO:41:

Gly Ser Trp Leu Arg Gly Pro Tyr Asp Met
1               5                   10

( 2 ) INFORMATION FOR SEQ ID NO:42:

( i ) SEQUENCE CHARACTERISTICS:
　　　　( A ) LENGTH: 10 amino acids
　　　　( B ) TYPE: amino acid
　　　　( D ) TOPOLOGY: linear ( i i ) MOLECULE TYPE: protein ( v ) FRAGMENT TYPE: internal ( x i ) SEQUENCE DESCRIPTION: SEQ ID NO:42:

Gly Thr Leu Gly Glu Gly Gly Tyr Asp Arg
1               5                   10

( 2 ) INFORMATION FOR SEQ ID NO:43:

( i ) SEQUENCE CHARACTERISTICS:
　　　　( A ) LENGTH: 16 amino acids
　　　　( B ) TYPE: amino acid
　　　　( D ) TOPOLOGY: linear ( i i ) MOLECULE TYPE: protein ( v ) FRAGMENT TYPE: internal ( x i ) SEQUENCE DESCRIPTION: SEQ ID NO:43:

Gly Trp Arg Ser Ser Arg Gly Val Val Trp Val Phe Ser Gly Asp Ala
1               5                   10                  15

( 2 ) INFORMATION FOR SEQ ID NO:44:

( i ) SEQUENCE CHARACTERISTICS:
　　　　( A ) LENGTH: 16 amino acids
　　　　( B ) TYPE: amino acid
　　　　( D ) TOPOLOGY: linear ( i i ) MOLECULE TYPE: protein ( v ) FRAGMENT TYPE: internal ( x i ) SEQUENCE DESCRIPTION: SEQ ID NO:44:

Gly Asp Trp Gly Trp Phe Thr Arg Val Ala Thr Trp Arg Pro Asp Val
1               5                   10                  15

( 2 ) INFORMATION FOR SEQ ID NO:45:

( i ) SEQUENCE CHARACTERISTICS:
　　　　( A ) LENGTH: 10 amino acids
　　　　( B ) TYPE: amino acid
　　　　( D ) TOPOLOGY: linear ( i i ) MOLECULE TYPE: protein ( v ) FRAGMENT TYPE: internal ( x i ) SEQUENCE DESCRIPTION: SEQ ID NO:45:

```
Gln Gln Tyr Leu Pro Gly Gly Arg Tyr Thr
 1               5                    10
```

( 2 ) INFORMATION FOR SEQ ID NO:46:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: protein ( v ) FRAGMENT TYPE: internal ( x i ) SEQUENCE DESCRIPTION: SEQ ID NO:46:

```
Gln Gln Tyr Arg Val Glu Gly Gln Thr
 1               5
```

( 2 ) INFORMATION FOR SEQ ID NO:47:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: protein ( v ) FRAGMENT TYPE: internal ( x i ) SEQUENCE DESCRIPTION: SEQ ID NO:47:

```
Gln Gln Tyr Gly Gly Ser Pro Trp
 1               5
```

( 2 ) INFORMATION FOR SEQ ID NO:48:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: protein ( v ) FRAGMENT TYPE: internal ( x i ) SEQUENCE DESCRIPTION: SEQ ID NO:48:

```
Gln Gln Tyr Ser Arg His Arg Phe Thr
 1               5
```

( 2 ) INFORMATION FOR SEQ ID NO:49:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: protein ( v ) FRAGMENT TYPE: internal ( x i ) SEQUENCE DESCRIPTION: SEQ ID NO:49:

```
Gln Gln Tyr Arg Tyr Pro Leu Ile Trp Thr
 1               5                    10
```

( 2 ) INFORMATION FOR SEQ ID NO:50:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: protein ( v ) FRAGMENT TYPE: internal ( x i ) SEQUENCE DESCRIPTION: SEQ ID NO:50:

Gln Gln Tyr Gly Ser Ser Leu Trp Thr
1               5

( 2 ) INFORMATION FOR SEQ ID NO:51:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: protein ( v ) FRAGMENT TYPE: internal ( x i ) SEQUENCE DESCRIPTION: SEQ ID NO:51:

Gln Gln Tyr Thr Arg Pro Gly Val Thr
1               5

( 2 ) INFORMATION FOR SEQ ID NO:52:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: protein ( v ) FRAGMENT TYPE: internal ( x i ) SEQUENCE DESCRIPTION: SEQ ID NO:52:

Gln Gln Tyr Ser Phe Lys Asn Trp Thr
1               5

( 2 ) INFORMATION FOR SEQ ID NO:53:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: protein ( v ) FRAGMENT TYPE: internal ( x i ) SEQUENCE DESCRIPTION: SEQ ID NO:53:

Gln Gln Tyr Gly Tyr Arg Lys Trp Thr
1               5

( 2 ) INFORMATION FOR SEQ ID NO:54:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: protein ( v ) FRAGMENT TYPE: internal ( x i ) SEQUENCE DESCRIPTION: SEQ ID NO:54:

Gln Gln Tyr Thr Pro Arg Arg Gly Ala Thr
1               5                   10

( 2 ) INFORMATION FOR SEQ ID NO:55:

( i ) SEQUENCE CHARACTERISTICS:

( A ) LENGTH: 10 amino acids
         ( B ) TYPE: amino acid
         ( D ) TOPOLOGY: linear ( i i ) MOLECULE TYPE: protein ( v ) FRAGMENT TYPE: internal ( x i ) SEQUENCE DESCRIPTION: SEQ ID NO:55:

Gln  Gln  Tyr  Thr  Pro  Arg  Val  Gly  His  Thr
   1                  5                        10

( 2 ) INFORMATION FOR SEQ ID NO:56:

( i ) SEQUENCE CHARACTERISTICS:
         ( A ) LENGTH: 10 amino acids
         ( B ) TYPE: amino acid
         ( D ) TOPOLOGY: linear ( i i ) MOLECULE TYPE: protein ( v ) FRAGMENT TYPE: internal ( x i ) SEQUENCE DESCRIPTION: SEQ ID NO:56:

Gln  Gln  Tyr  Lys  Tyr  Gly  Arg  Gly  Met  Thr
   1                  5                        10

( 2 ) INFORMATION FOR SEQ ID NO:57:

( i ) SEQUENCE CHARACTERISTICS:
         ( A ) LENGTH: 9 amino acids
         ( B ) TYPE: amino acid
         ( D ) TOPOLOGY: linear ( i i ) MOLECULE TYPE: protein ( v ) FRAGMENT TYPE: internal ( x i ) SEQUENCE DESCRIPTION: SEQ ID NO:57:

Gln  Gln  Tyr  Gly  Lys  Lys  Gln  Trp  Thr
   1                  5

( 2 ) INFORMATION FOR SEQ ID NO:58:

( i ) SEQUENCE CHARACTERISTICS:
         ( A ) LENGTH: 9 amino acids
         ( B ) TYPE: amino acid
         ( D ) TOPOLOGY: linear ( i i ) MOLECULE TYPE: protein ( v ) FRAGMENT TYPE: internal ( x i ) SEQUENCE DESCRIPTION: SEQ ID NO:58:

Gln  Gln  Tyr  Val  Arg  Arg  Ser  Gly  Thr
   1                  5

( 2 ) INFORMATION FOR SEQ ID NO:59:

( i ) SEQUENCE CHARACTERISTICS:
         ( A ) LENGTH: 10 amino acids
         ( B ) TYPE: amino acid
         ( D ) TOPOLOGY: linear ( i i ) MOLECULE TYPE: protein ( v ) FRAGMENT TYPE: internal ( x i ) SEQUENCE DESCRIPTION: SEQ ID NO:59:

Gln  Gln  Tyr  Gly  Lys  Arg  Ser  Pro  Val  Thr
   1                  5                        10

( 2 ) INFORMATION FOR SEQ ID NO:60:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: protein ( v ) FRAGMENT TYPE: internal ( x i ) SEQUENCE DESCRIPTION: SEQ ID NO:60:

```
Gln Gln Tyr Ala Arg Ala Thr Gly Leu Thr
 1               5                  10
```

( 2 ) INFORMATION FOR SEQ ID NO:61:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: protein ( v ) FRAGMENT TYPE: internal ( x i ) SEQUENCE DESCRIPTION: SEQ ID NO:61:

```
Gln Gln Tyr Ser Arg Phe Val Ser Arg Thr
 1               5                  10
```

( 2 ) INFORMATION FOR SEQ ID NO:62:

( i ) SEQUENCE CHARACTERISTICS:
        ( A ) LENGTH: 280 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:62:

```
GAGCTCACCC AGTCTCCATC CTCCCTGTCT GCATCTGTAG GAGACAGAGT CACCATCACT      60
TGCCGGGCAA GTCAGCGCAT TAGCAGCTAT TTAAATTGGT ATCAGCAGGA ACCAGGGGAA     120
GCCCCTAAGC TCCTGATCTA TGCTGCATCC AGGTTTGCAA AGTGGGGTCC CATCAAGGTT     180
CAGTGGCAGT GGATCTGGGA CAGATTTCAC TCTCACCATC AGCAGTCTGC AACCTGAAGA     240
TTTTGCAACT TACTACTGTC AACAGAGTTA CAGTACCCCG                           280
```

( 2 ) INFORMATION FOR SEQ ID NO:63:

( i ) SEQUENCE CHARACTERISTICS:
        ( A ) LENGTH: 124 amino acids
        ( B ) TYPE: amino acid
        ( D ) TOPOLOGY: linear ( i i ) MOLECULE TYPE: protein ( x i ) SEQUENCE DESCRIPTION: SEQ ID NO:63:

```
Leu Glu Ser Gly Gly Asp Leu Val Gln Pro Gly Gly Ser Leu Arg Leu
 1               5                  10                  15
Ser Cys Glu Ala Ser Gly Phe Thr Phe Gly Ser Tyr Ala Met Thr Trp
                20                  25                  30
Val Arg Gln Ala Pro Gly Lys Gly Leu Glu Trp Val Ser Ser Pro Ser
                35                  40                  45
Ala Asn Gly Asp Phe Ala Tyr Tyr Ala Asp Ser Val Lys Gly Arg Phe
```

|  | 50 |  |  |  |  | 55 |  |  |  |  | 60 |  |  |  |
|---|---|---|---|---|---|---|---|---|---|---|---|---|---|---|
| Thr | Ile | Ser | Arg | Asp | Lys | Ser | Lys | His | Thr | Leu | Phe | Leu | Gln | Met | His |
| 65 |  |  |  |  | 70 |  |  |  |  | 75 |  |  |  |  | 80 |

Ser Leu Arg Val Glu Asp Thr Ala Val Tyr Tyr Cys Ala Lys Ala Gly
              85                    90                    95

Arg Ile Leu Gly Val Val Leu Trp Tyr Ser Leu Tyr Tyr Gly Phe Asp
             100                   105                  110

Val Trp Gly Gln Gly Thr Thr Val Thr Val Ser Ser
             115             120

( 2 ) INFORMATION FOR SEQ ID NO:64:

( i ) SEQUENCE CHARACTERISTICS:
      ( A ) LENGTH: 118 amino acids
      ( B ) TYPE: amino acid
      ( D ) TOPOLOGY: linear ( i i ) MOLECULE TYPE: protein ( x i ) SEQUENCE DESCRIPTION: SEQ ID NO:64:

Leu Glu Gln Ser Gly Ala Glu Val Lys Lys Pro Gly Ala Ser Val Lys
 1               5                  10                  15

Val Ser Cys Lys Ala Ser Gly Tyr Asn Phe Asn Ser His Asp Ile Asn
             20                  25                  30

Trp Val Arg Gln Ala Thr Gly Gln Gly Leu Glu Trp Ile Gly Trp Ile
             35                  40                  45

Thr Asn Arg Gly Thr Thr Ser Arg Tyr Ala Gln Lys Phe Gln Gly Arg
 50                           55                  60

Val Thr Met Thr Arg Asp Ala Ser Ile Ser Thr Val Tyr Met Glu Leu
 65                           70                  75                  80

Ser Ser Leu Thr Ser Glu Asp Thr Ala Val Tyr Tyr Cys Ala Arg Gly
             85                  90                  95

Ala Gly Ala Gly Gly Thr Trp Gly Met Asp Val Trp Gly Gln Gly Thr
             100                 105                 110

Thr Val Ile Val Ser Ser
             115

( 2 ) INFORMATION FOR SEQ ID NO:65:

( i ) SEQUENCE CHARACTERISTICS:
      ( A ) LENGTH: 119 amino acids
      ( B ) TYPE: amino acid
      ( D ) TOPOLOGY: linear ( i i ) MOLECULE TYPE: protein ( x i ) SEQUENCE DESCRIPTION: SEQ ID NO:65:

Gln Val Lys Leu Leu Glu Ser Gly Ala Glu Val Lys Lys Pro Gly Ala
 1               5                  10                  15

Ser Val Lys Val Ser Cys Lys Ala Ser Gly Tyr Thr Phe Thr Gly His
             20                  25                  30

Tyr Met His Trp Val Arg Gln Ala Pro Gly Gln Gly Leu Glu Trp Ile
             35                  40                  45

Gly Trp Ile Ser Pro Asn Arg Gly Ala Thr Arg Phe Ala Gln Lys Phe
 50                           55                  60

Gln Gly Arg Val Thr Met Thr Ser Asp Thr Ser Ile Asn Thr Val Tyr
 65                           70                  75                  80

Met Glu Leu Ser Gly Leu Arg Phe Asp Asp Thr Ala Val Tyr Tyr Cys
             85                  90                  95

```
        Ala  Thr  Thr  Arg  Thr  Ala  Tyr  Tyr  Gly  Met  Asp  Val  Trp  Gly  Gln  Gly
                       100                      105                      110

Thr  Thr  Val  Thr  Val  Ser  Ser
                       115
```

( 2 ) INFORMATION FOR SEQ ID NO:66:

( i ) SEQUENCE CHARACTERISTICS:
        ( A ) LENGTH: 107 amino acids
        ( B ) TYPE: amino acid
        ( D ) TOPOLOGY: linear ( i i ) MOLECULE TYPE: protein ( x i ) SEQUENCE DESCRIPTION: SEQ ID NO:66:

```
        Glu  Met  Thr  Gln  Ser  Pro  Ser  Ser  Leu  Ser  Ala  Ser  Val  Gly  Asp  Arg
        1                   5                        10                       15

Val  Thr  Ile  Thr  Cys  Arg  Ala  Ser  Gln  Ser  Ile  Ser  Ser  Tyr  Ile  Asn
                       20                      25                       30

Trp  Tyr  Gln  Gln  Lys  Pro  Gly  Lys  Ala  Pro  Lys  Leu  Leu  Ile  Tyr  Ala
                       35                      40                       45

Ala  Ser  Thr  Leu  Gln  Ser  Gly  Val  Pro  Ser  Arg  Phe  Ser  Gly  Ser  Gly
                  50                      55                       60

Ser  Gly  Thr  Asp  Phe  Thr  Leu  Thr  Ile  Ser  Ser  Leu  Gln  Pro  Glu  Asp
        65                       70                       75                       80

Phe  Ala  Thr  Tyr  Tyr  Cys  Gln  Gln  Ser  Tyr  Ser  Thr  Pro  Phe  Thr  Phe
                            85                       90                       95

Cys  Pro  Gly  Thr  Lys  Val  Asp  Ile  Lys  Arg  Thr
                       100                      105
```

( 2 ) INFORMATION FOR SEQ ID NO:67:

( i ) SEQUENCE CHARACTERISTICS:
        ( A ) LENGTH: 107 amino acids
        ( B ) TYPE: amino acid
        ( D ) TOPOLOGY: linear ( i i ) MOLECULE TYPE: protein ( x i ) SEQUENCE DESCRIPTION: SEQ ID NO:67:

```
        Glu  Met  Thr  Gln  Ser  Pro  Ser  Ser  Leu  Ser  Ala  Ser  Val  Gly  Asp  Arg
        1                   5                        10                       15

Val  Thr  Ile  Thr  Cys  Arg  Ala  Ser  Gln  Arg  Ile  Ser  Ser  Tyr  Ile  Asn
                       20                      25                       30

Trp  Tyr  Gln  Gln  Glu  Lys  Pro  Gly  Ala  Pro  Lys  Leu  Leu  Ile  Tyr  Ala
                       35                      40                       45

Ala  Ser  Ser  Leu  Gln  Ser  Gly  Val  Pro  Ser  Arg  Phe  Ser  Gly  Ser  Gly
                  50                      55                       60

Ser  Gly  Thr  Asp  Phe  Thr  Leu  Thr  Ile  Ser  Ser  Leu  Gln  Pro  Glu  Asp
        65                       70                       75                       80

Phe  Ala  Thr  Tyr  Tyr  Cys  Gln  Gln  Ser  Tyr  Ser  Thr  Pro  Tyr  Thr  Phe
                            85                       90                       95

Cys  Gln  Gly  Thr  Lys  Leu  Glu  Ile  Lys  Arg  Thr
                       100                      105
```

( 2 ) INFORMATION FOR SEQ ID NO:68:

( i ) SEQUENCE CHARACTERISTICS:
        ( A ) LENGTH: 109 amino acids
        ( B ) TYPE: amino acid
        ( D ) TOPOLOGY: linear ( i i ) MOLECULE TYPE: protein ( x i ) SEQUENCE DESCRIPTION: SEQ ID NO:68:

| Glu | Leu | Val | Met | Thr | Gln | Ser | Pro | Ser | Ser | Leu | Ser | Ala | Ser | Glu | Gly |
|---|---|---|---|---|---|---|---|---|---|---|---|---|---|---|---|
| 1 | | | | 5 | | | | | 10 | | | | | 15 | |

| Asp | Thr | Val | Thr | Ile | Thr | Cys | Arg | Ala | Ser | Glu | Asn | Ile | Ser | Arg | Tyr |
|---|---|---|---|---|---|---|---|---|---|---|---|---|---|---|---|
| | | | 20 | | | | | 25 | | | | | 30 | | |

| Ser | Asn | Trp | Tyr | Gln | Gln | Gln | Pro | Gly | Lys | Ala | Pro | Lys | Leu | Leu | Ile |
|---|---|---|---|---|---|---|---|---|---|---|---|---|---|---|---|
| | | | 35 | | | | | 40 | | | | | 45 | | |

| Ser | Ala | Ala | Ser | Thr | Leu | Gln | Ser | Gly | Val | Pro | Ser | Arg | Phe | Ser | Gly |
|---|---|---|---|---|---|---|---|---|---|---|---|---|---|---|---|
| | 50 | | | | | 55 | | | | | 60 | | | | |

| Ser | Gly | Ser | Gly | Thr | His | Phe | Thr | Leu | Thr | Ile | Asn | Ser | Leu | Gln | Pro |
|---|---|---|---|---|---|---|---|---|---|---|---|---|---|---|---|
| 65 | | | | | 70 | | | | | 75 | | | | | 80 |

| Gly | Asp | Phe | Ala | Thr | Tyr | Tyr | Cys | Gln | Gln | Thr | Tyr | Ser | Ser | Pro | Phe |
|---|---|---|---|---|---|---|---|---|---|---|---|---|---|---|---|
| | | | | 85 | | | | | 90 | | | | | 95 | |

| Thr | Phe | Cys | Gln | Gly | Thr | Lys | Leu | Glu | Ile | Lys | Arg | Thr |
|---|---|---|---|---|---|---|---|---|---|---|---|---|
| | | | 100 | | | | | 105 | | | | |

( 2 ) INFORMATION FOR SEQ ID NO:69:

( i ) SEQUENCE CHARACTERISTICS:
( A ) LENGTH: 109 amino acids
( B ) TYPE: amino acid
( D ) TOPOLOGY: linear ( i i ) MOLECULE TYPE: protein ( x i ) SEQUENCE DESCRIPTION: SEQ ID NO:69:

| Glu | Leu | Val | Met | Thr | Gln | Ser | Pro | Ser | Ser | Leu | Ser | Ala | Ser | Val | Gly |
|---|---|---|---|---|---|---|---|---|---|---|---|---|---|---|---|
| 1 | | | | 5 | | | | | 10 | | | | | 15 | |

| Asp | Arg | Val | Thr | Ile | Thr | Cys | Arg | Ala | Ser | Gln | Thr | Ile | Gly | Thr | Tyr |
|---|---|---|---|---|---|---|---|---|---|---|---|---|---|---|---|
| | | | 20 | | | | | 25 | | | | | 30 | | |

| Ile | Asn | Trp | Tyr | Gln | Gln | Lys | Pro | Gly | Glu | Ala | Pro | Lys | Leu | Leu | Ile |
|---|---|---|---|---|---|---|---|---|---|---|---|---|---|---|---|
| | | | 35 | | | | | 40 | | | | | 45 | | |

| Tyr | Thr | Ala | Ser | Thr | Leu | Gln | Ser | Gly | Val | Pro | Ser | Arg | Phe | Arg | Gly |
|---|---|---|---|---|---|---|---|---|---|---|---|---|---|---|---|
| | 50 | | | | | 55 | | | | | 60 | | | | |

| Ser | Gly | Ser | Gly | Thr | Asp | Phe | Thr | Leu | Thr | Ile | Ser | Ser | Leu | Gln | Pro |
|---|---|---|---|---|---|---|---|---|---|---|---|---|---|---|---|
| 65 | | | | | 70 | | | | | 75 | | | | | 80 |

| Glu | Asp | Phe | Ala | Thr | Tyr | Tyr | Cys | Gln | Gln | Ser | Tyr | Ser | Thr | Pro | Trp |
|---|---|---|---|---|---|---|---|---|---|---|---|---|---|---|---|
| | | | | 85 | | | | | 90 | | | | | 95 | |

| Thr | Phe | Cys | Gln | Gly | Thr | Lys | Val | Glu | Ile | Lys | Arg | Thr |
|---|---|---|---|---|---|---|---|---|---|---|---|---|
| | | | 100 | | | | | 105 | | | | |

( 2 ) INFORMATION FOR SEQ ID NO:70:

( i ) SEQUENCE CHARACTERISTICS:
( A ) LENGTH: 110 amino acids
( B ) TYPE: amino acid
( D ) TOPOLOGY: linear ( i i ) MOLECULE TYPE: protein ( x i ) SEQUENCE DESCRIPTION: SEQ ID NO:70:

| Glu | Leu | Val | Met | Thr | Gln | Ser | Pro | Ser | Ser | Leu | Ser | Ala | Ser | Val | Gly |
|---|---|---|---|---|---|---|---|---|---|---|---|---|---|---|---|
| 1 | | | | 5 | | | | | 10 | | | | | 15 | |

| Asp | Arg | Val | Thr | Ile | Ser | Gly | Cys | Arg | Ala | Ser | Gln | Asn | Ile | Gly | Lys |
|---|---|---|---|---|---|---|---|---|---|---|---|---|---|---|---|
| | | | 20 | | | | | 25 | | | | | 30 | | |

| Tyr | Ile | Asn | Trp | Tyr | Arg | Gln | Lys | Pro | Gly | Lys | Ala | Pro | Glu | Leu | Leu |
|---|---|---|---|---|---|---|---|---|---|---|---|---|---|---|---|
| | | | 35 | | | | | 40 | | | | | 45 | | |

| Ile | Tyr | Gly | Thr | Ser | Thr | Leu | Gln | Ser | Gly | Val | Pro | Ser | Arg | Phe | Ser |

-continued

|  |  |  |  |  | 50 |  |  |  | 55 |  |  |  |  | 60 |  |
|---|---|---|---|---|---|---|---|---|---|---|---|---|---|---|---|
| Gly | Ser | Gly | Ser | Gly | Thr | Asp | Phe | Thr | Leu | Thr | Ile | Ser | Ser | Leu | Gln |
| 65 |  |  |  |  | 70 |  |  |  | 75 |  |  |  |  |  | 80 |
| Pro | Glu | Asp | Phe | Ala | Thr | Tyr | Tyr | Cys | Gln | Gln | Ser | Tyr | Ser | Thr | Pro |
|  |  |  |  | 85 |  |  |  |  | 90 |  |  |  |  | 95 |  |
| Trp | Thr | Phe | Cys | Gln | Gly | Thr | Lys | Val | Glu | Ile | Lys | Arg | Thr |  |  |
|  |  |  | 100 |  |  |  |  | 105 |  |  |  |  | 110 |  |  |